United States Patent
Böhlendorf et al.

[11] Patent Number: 4,997,820
[45] Date of Patent: Mar. 5, 1991

[54] MICROBICIDES

[75] Inventors: Bettina Böhlendorf, Braunschweig, Fed. Rep of Germany; Norbert Bedorf, Königslutter, Fed. Rep. of Germany; Gerhard Höfle, Braunschweig, Fed. Rep. of Germany; Dietmar Schummer, Braunschweig, Fed. Rep. of Germany; Marius Sutter, Basel, Switzerland.

[73] Assignees: Gesellschaft fur Biotechnologische Forschung mbH, Fed. Rep. of Germany; Ciba-Geigy Corporation, Ardsley, N.Y.

[21] Appl. No.: 405,376

[22] Filed: Sep. 8, 1989

[30] Foreign Application Priority Data

Sep. 9, 1988 [CH] Switzerland ............... 3375/88

[51] Int. Cl.$^5$ ............... A01N 55/00; C07D 335/02; C07D 321/00
[52] U.S. Cl. ............................. 514/63; 514/75; 514/149; 514/184; 514/186; 514/191; 514/432; 514/444; 514/450; 549/28; 549/60; 549/208; 549/218; 549/214; 549/267
[58] Field of Search ............... 549/267, 28, 60, 214, 549/208, 218; 514/450, 432, 149, 63, 75, 186, 191, 444

Primary Examiner—Glennon H. Hollrah
Assistant Examiner—Amelia A. Owens
Attorney, Agent, or Firm—George R. Dohmann; Edward McC. Roberts

[57] ABSTRACT

Novel macrocyclic compounds of the formual I

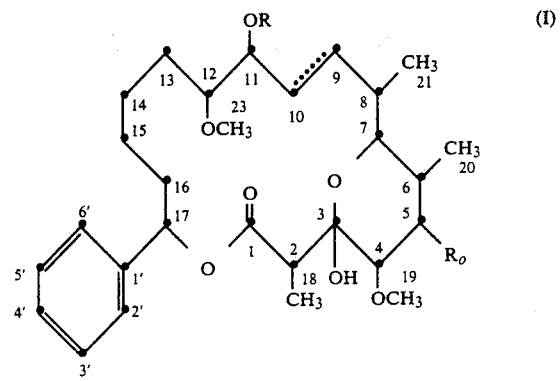

where the dotted line in the 9,10-position is a saturated bond or a double bond, alternatively, and R is hydrogen, methyl or certain acyl radicals, and $R_o$ is hydrogen, halogen, azido, thiol, hydroxyl or —OY, where Y is, among other radicals, an ether radical, a silyl group, a sulfonyl group, a sugar radical or a (thiol)acyl radical, and R being methyl if there is a double bond in the 9,10-position, have microbicidal properties for the control of phytopathogenic microorganisms. They can be employed in the customary formulation for the control of plant disease.

17 Claims, No Drawings

MICROBICIDES

The present invention relates to a macrocyclic compound of the formula I, to a process for its preparation, and to its use for controlling plant diseases, as well as to phytomicrobicidal agents which contain this compound as the active substance.

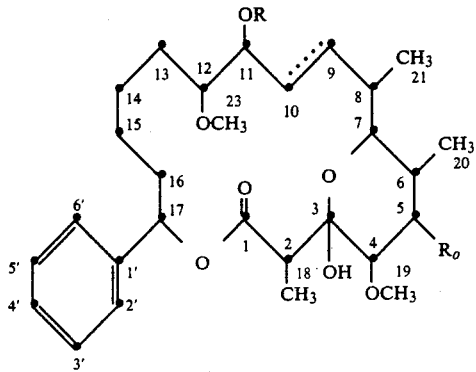

In this formula, the dotted line in the 9,10-position is a saturated bond or a double bond alternatively, while R is hydrogen, $CH_3$ or —COA, where A is hydrogen or $C_3$-$C_6$cycloalkyl, or is $C_1$-$C_6$alkyl which is unsubstituted or substituted by halogen or $C_1$-$C_3$alkoxy, and $R_o$ is hydrogen, halogen, —$N_3$, —SH, —OH or —OY, where Y, alternatively, (a) is a $C_3$-$C_6$alkenyl or alkynyl group, an unsubstituted or substituted $C_1$-$C_6$alkyl group, an alkoxyalkoxyalkyl group having up to 10 C atoms, a $C_3$-$C_6$cycloalkyl group or an unsubstituted or substituted phenyl group, or (b) is a silyl group —$SiR_1R_2R_3$, in which $R_1$-$R_3$ independently are alkyl, phenyl, benzyl or $C_3$-$C_6$cycloalkyl, or (c) is —$SO_2Z$, where Z is the group —OM, in which M is hydrogen or the mole equivalent of a metal, or where Z is $C_1$-$C_6$alkyl or unsubstituted or substituted aryl; or (d) is a group

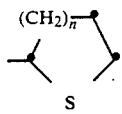

where n is 1 or 2 or is a group

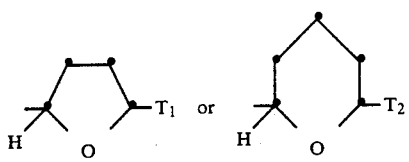

which is unsubstituted or, like a furanose or pyranose, completely or partly substituted by —OH and in which $T_1$ is hydrogen, —OH, —$CH_2OH$ or —CHOH—$CH_2OH$ and $T_2$ is hydrogen, —OH or —$CH_2OH$, or (e) is a (thio)acyl group —CO—B or —CS—B, where B is hydrogen or unsubstituted or substituted $C_1$-$C_6$alkyl, or is $C_2$-$C_6$alkenyl, $C_2$-$C_6$alkynyl, $C_3$-$C_6$cycloalkyl or unsubstituted or substituted phenyl, or one of the groups —$N(R_4)(R_5)$, —$OR_6$ or —$SR_6$, $R_4$ and $R_5$ independently of one another are hydrogen, $C_1$-$C_6$alkyl, $C_1$-$C_6$haloalkyl, $C_3$-$C_6$alkenyl, $C_3$-$C_6$alkynyl, $C_3$-$C_6$cycloalkyl or phenyl, and $R_6$ is $C_1$-$C_6$alkyl, $C_3$-$C_6$cycloalkyl or phenyl, with the proviso that R is methyl if a double bond is present in the 9,10-position, and that R is the group —COA if $R_o$ is an OH group.

If Y is a substituted $C_1$-$C_6$alkyl group, possible substituents are halogen, hydroxyl, $C_1$-$C_6$alkoxy, $C_1$-$C_6$alkylthio, carboxyl (=COOH), amino, $C_3$-$C_6$cycloalkyl, phenyl or substituted phenyl, or phenoxy or substituted phenoxy. In general, however, an alkyl group contains a maximum of one or two aromatic rings.

A substituted phenyl or phenoxy group can be monosubstituted or polysubstituted by identical or different substituents, such as $C_1$-$C_4$alkyl, halogen, hydroxyl, $C_1$-$C_4$alkoxy, $CF_3$ or $NO_2$, it being self-evident for those skilled in the art that space-filling substituents, such as tert-butyl, occur not more than three times, or substituents which tend to disintegrate, such as $NO_2$, occur not more than twice in the phenyl ring, while other substituents such as fluorine or methyl can be represented up to five times.

Halogens are to be understood as meaning fluorine, chlorine, bromine or iodine.

Aryl is phenyl, naphthyl or diphenyl. $C_3$-$C_6$cycloalkyl is to be understood as meaning cyclopropyl, cyclobutyl, cyclopentyl and cyclohexyl.

Depending on the chain length, alkyl is to be understood as meaning methyl, ethyl, propyl, butyl, amyl, hexyl, heptyl, octyl, nonyl, decyl as well as their isomers, for example isopropyl, isobutyl, sec-butyl, tert-butyl, neopentyl etc.

An alkyl radical which is substituted by halogen is a monohalogenated to perhalogenated alkyl substituent, such as $CHCl_2$, $CH_2Cl$, $CCl_3$, $CF_3$, $CH_2F$, $CH_2Br$, $CH_2CH_2Cl$, CHF—$CH_3$, $CHBr_2$ etc.

Examples of alkyl radicals which are monosubstituted or polysubstituted by alkoxy, also in the sense of an alkoxyalkoxy substitution, may be —$CH_2OCH_3$, —$CH_2CH_2OCH_3$, —$CH_2CH(CH_3)OCH_3$, —$CH_2OC_2H_5$, —$CH_2OC_3H_7$—i, —$CH_2CH_2CH_2OCH_3$, —$CH_2OCH_2OCH_3$, $CH_2CH_2OCH_2OCH_3$, —$CH_2OCH_2CH_2OCH_3$, —$CH_2OCH_2OC_2H_5$, —$C(CH_3)_2$—$CH_2OCH_3$, —$CH(CH_3)OCH_2OC_3H_7$—i, —CH(OCH_3)—$CH_2OCH_3$ and other branched or unbranched radicals.

Alkenyl is an aliphatic hydrocarbon radical having one double bond, for example vinyl, propen-1-yl, allyl, buten-1-yl, buten-2-yl, hexen-2-yl etc.

Alkynyl is an aliphatic hydrocarbon radical having one triple bond, for example ethynyl, propyn-1-yl, propargyl, butyn-1-yl etc.

The tetrahydrofurans and tetrahydropyrans mentioned for Y under (d) as well as their thio-analogues include monosaccharides, for example glucose, fructose, altrose, mannose, sorbose, gulose, idose, allose, galactose, ribose, arabinose, xylose, lyxose, erythrose, threose, rhamnose, altrose or talose.

A saccharide can be bonded in the 5-position of the compounds of the formula I as an α-anomer or β-anomer. The present invention relates to both types of bonding.

In the event that Y is a group —CO—$N(R_4)(R_5)$ or —CO—$OR_6$ or —CO—$SR_6$ respectively, as defined under (e), the compounds of the formula I are carbamic esters or carbonic esters or thiocarbonic esters, respectively. Possible metals for the substituent M are, in particular, alkali metals and alkaline earth metals, such as Li, Na, K, Ca or Mg, as well as Al, Co, Ni, Zn or Cu.

Formula I comprises all possible stereoisomers.

The compounds of the formula I are derived from the basic structure of novel macrocyclic compounds of the formula below, called "soraphen A" and "soraphen B"

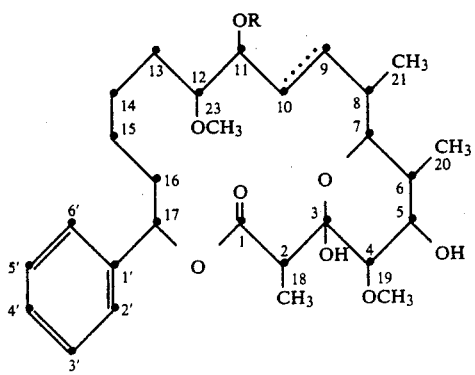

In this formula, R is methyl if there is a double bond in the 9,10-position (=soraphen A), or R is hydrogen if there is a single bond in the 9,10-position (=soraphen B). The formula I furthermore comprises derivatives of 9,10-dihydro-soraphen A, which is obtained by hydrogenation of soraphen A.

Due to the physicochemical data, it is assumed that the following configuration can be assigned to these two preparations:

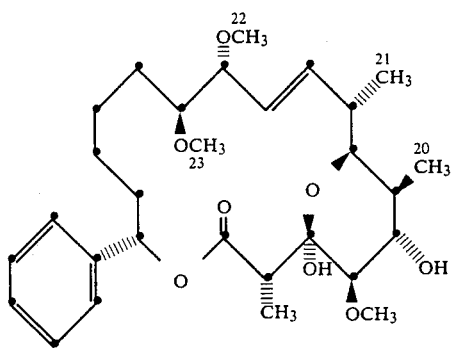

Soraphen A

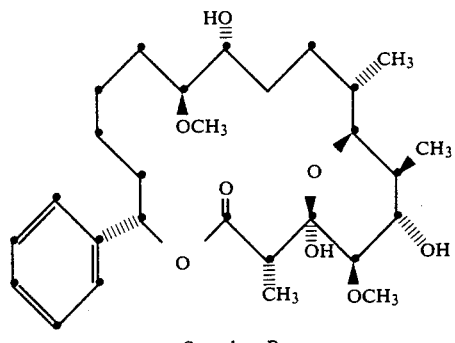

Soraphen B

Soraphen A and soraphen B are obtained by macrobiological cultivation of a Sorangium (Polyangium) cellulosum strain "So ce 26". This strain was deposited on Mar. 5, 1987, at the "National Collection of Industrial and Marine Bacteria (NCIB)", Torry Research Station, Aberdeen, Great Britain, in compliance with the provisions of the Budapest Convention, deposit No. NCIB 12,411. Sorangium cellulosum belongs to the order of the Myxobacterales, sub-order Sorangineae, family Polyangiaceae.

"So ce 26" itself, or mutants or recombinants, are the subject-matter of European Patent Application EP-A-0,282,455. The strain can be cultured by conventional biological methods, for example in agitated cultures or in fermenters, using nutrient media having a pH of 6-8, at 10°-35° C. The procedure is aerobic. The conditions for culturing the microrganism are introduced into the present description as a reference to EP-A-0,282,455.

In compounds of the formula I of the present invention, or in the case of corresponding intermediates, the reactivity of the hydroxyl group in the 5-position is different to that of a hydroxyl group in the 11-position of the molecule. This allows access to compounds of the formula I which are, for example, partially acylated or acylated by different acyl radicals in these positions, starting from "soraphen A", "9,10-dihydro-soraphen A" or "soraphen B". Alternatively, acylation products may be separated from each other for example by chromatography.

An important sub-group of compounds of the formula I embraces those in which R is $CH_3$ and $R_o$ is halogen, $-N_3$, $-SH$, $-OH$ or $-OY$, where Y has the meanings mentioned under (a), (b), (c), (d) and (e). Here and below, this group shall be designated sub-group IA.

From amongst the compounds of sub-group IA, those in which Y has the meaning mentioned under (a) represent a particular group (=sub-group IB).

Another important sub-group embraces those of the formula IA in which Y has the meaning mentioned under (b) (=sub-group IC).

A further important sub-group embraces those of the formula IA in which Y has the meaning mentioned under (d) (=sub-group ID), in particular those in which Y is a tetrahydrofuranyl or tetrahydropyranyl ring which is substituted by hydroxyl and $-CH_2OH$ (=sub-group IDD).

A further important sub-group embraces those of the formula IA in which Y is acylated as mentioned under (e) (=sub-group IE).

Another series of important compounds of the formula I embraces those in which R is hydrogen or the group $-COA$, where A is hydrogen or $C_3-C_6$cycloalkyl, or is $C_1-C_6$alkyl which is unsubstituted or substituted by halogen or $C_1-C_3$alkoxy, while $R_o$ is hydrogen, $N_3$, halogen, OH or $-SH$. Here and below, this group will be designated sub-group IIa.

From amongst these, those in which A is a $C_1-C_4$alkyl group which is unsubstituted or substituted by halogen or $C_1-C_3$alkoxy represent an important group (=sub-group IIB).

The individual compounds which are preferred as microbicides include:
soraphen A 5-propionate (Compound No. 6)
soraphen A 5-butyrate (Compound No. 7)
soraphen A 5-isobutyrate (Compound No. 8)
soraphen A 5-acetate (Compound No. 4)
soraphen A 5-formate (Compound No. 1)
soraphen A 5-trichloroacetate (Compound No. 25)
soraphen A 5-succinate (Compound No. 55)
soraphen A 5-tiglate (Compound No. 49)
soraphen A 5-methoxyacetate (Compound No. 47)

soraphen A 5-β-D-glucopyranoside (Compound No. 136) and
soraphen A 5-(5R)-β-D-glucopyranoside (Compound No. 136)
soraphen A 5-pivalate (Compound No. 171)
9,10-dihydro-soraphen A 5-methoxyacetate (Compound No. 113)
9,10-dihydro-soraphen A 5-formate (Compound No. 18)
9,10-dihydro-soraphen A 5-trichloroacetate (Compound No. 175)
9,10-dihydro-soraphen A 5-β-D-glucopyranoside (Compound No. 124) and
9,10-dihydro-soraphen A 5-(5R)-β-D-glucopyranoside (Compound No. 124)
soraphen B 5,11-diacetate (Compound No. 11)
soraphen B 5-formate (Compound No. 2)
soraphen B 5,11-diformate (Compound No. 3)
soraphen B 5-trichloroacetate (Compound No. 176)
soraphen A 5-aminoacetate (Compound No. 53)
soraphen B 5-aminoacetate (Compound No. 178)
9,10-dihydro-soraphen A 5-aminoacetate (Compound No. 177).

Derivatives in the 5- and 11-positions, respectively, can be obtained from compounds of the formula I starting from "soraphen A" or "soraphen B", by methods which are likewise the subject-matter of the present invention.

The process for the preparation of compounds of the formula I comprises etherification, silylation or acylation of the 5-hydroxyl group in "soraphen A", in "9,10-dihydro-soraphen A" or in "soraphen B" and/or acylation of the 11-hydroxyl group in "soraphen B".

As starting materials for obtaining derivatives, these three preparations "soraphen A", "9,10-dihydro-soraphen A" and "soraphen B" shall be designated "soraphen" here and below, to simplify matters.

Customary acylation of an OH group with the corresponding (thio)carboxylic acid or with a corresponding acyl halide, acyl anhydride or ester, or with the corresponding sulfonic acid or its acyl halide, or reaction of an OH group with the appropriately substituted silane derivative of the formula

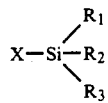

gives all those derivatives in which R is the group —COA and $R_o$ is the group —OY, respectively, in which Y has one of the meanings mentioned under (b), (c) or (e), the term acyl halide, which also includes sulfonyl halide, representing acyl chloride or acyl bromide, and X being a silyl leaving group. The silyl leaving groups S include, for example, bromide, chloride and trifluoromethanesulfonate. This enumeration does not represent any limitation. Further typical silyl leaving groups are known to those skilled in the art. Possible suitable silyl groups —$SiR_1R_2R_3$ are, for example, trimethylsilyl, diphenyl-tert-butylsilyl, bis(isopropyl)methylsilyl, triphenylsilyl etc., and in particular tert-butyldimethylsilyl.

O-Acylations and O-silylations are carried out in an anhydrous medium, preferably in inert solvents and particularly preferably in aprotic solvents. The reaction advantageously proceeds in the temperature range of 0° C. to 80° C., preferably at 10° C. to 50° C.

It is preferred to add an organic base. Bases which may be mentioned are, for example, tertiary amines, such as triethylamine, triethylenediamine, triazole and preferably pyridine, imidazole or 1,8-diazabicyclo[5.4.0]undec-7-ene (DBU).

Examples of suitable solvents are: ethers and ether-type compounds, such as dialkyl ethers (diethyl ether, diisopropyl ether), tert-butyl methyl ether, dimethoxyethane, dioxane, tetrahydrofuran, anisole, etc.); halogenated hydrocarbons, such as chlorobenzene, methylene chloride, ethylene chloride, chloroform, carbon tetrachloride, tetrachloroethylene, etc.; or sulfoxides, such as dimethyl sulfoxide, it being also possible for aromatic or aliphatic hydrocarbons, such as benzene, toluene, xylenes, petroleum ether, ligroin, cyclohexane etc., to be present. In some cases, it can be advantageous for the reactions to be carried out under a protective gas atmosphere (for example argon, helium, nitrogen, etc.) and/or in absolute solvents.

If a free carboxylic acid or sulfonic acid is employed as a reactant for the acylation, this reaction is expediently carried out in the presence of water-eliminating reagents. For example, the process is carried out in the presence of dicyclohexylcarbodiimide and pyridine, or in the presence of dialkyl azodicarboxylates and triphenylphosphine.

If acid halides or acid anhydrides are employed in the acylation, it is advantageous to add a neutralizing agent. Reagents which are expedient are tertiary amines, such as trialkylamines, pyridine or pyridine bases, such as 4-dimethylaminopyridine, and they can also serve as solvents in some cases.

Should it be desired to introduce a sulfonic acid group or its salt —$SO_3M$ into the 5-position, soraphen is allowed to react with the [$SO_3$/triethylamine] complex in the presence of a base, such as alkali metal hydroxide, alkali metal carbonate or NaH, at 0° to 150° C., it being advantageous to add a solvent, such as halohydrocarbon, for example chloroform [W. B. Hardy et al. J. Am. Chem. Soc. 74, 5212 (1952)].

Compounds of the formula I which have a sugar radical bonded in the 5-position to the oxygen atom are prepared by one of the linking methods used in sugar chemistry, for example by Koenigs-Knorr synthesis, the Ag-triflate process, the ortho ester process, the phenylthio synthesis or the 2-pyridylthio synthesis.

(A) In the Koenigs-Knorr synthesis or the silver-triflate process, the 5-hydroxyl group of the compound of the formula I ($R_o$=OH) can be obtained using the sugar radical to be introduced, in which all the OH groups are protected, for example by acetylation, with the exception of the chlorine- or bromine-substituted 1-OH group of the sugar radical, in the temperature range of −30° C. to +60° C., preferably −5° C. to +30° C., with the exclusion of light and in the presence of a silver salt or mercury salt as the condensation agent.

The protected 1-chloro- or 1-bromo-sugar is added to soraphen in at least equimolar amounts, but preferably in 1.5- to 3-fold excess.

The silver salt used may be freshly precipitated $Ag_2O$, $Ag/Ag_2O$ precipitated on $Al_2O_3$, but preferably $Ag_2CO_3$ or $CF_3COOAg$. Silver trifluoromethanesulfonate (=Ag-triflate =$CF_3$—$SO_3Ag$), in whose presence the glycosidation proceeds rapidly even at temperatures below °C., is particularly preferred. A tert-amine (triethylamine, diisopropylethylamine, diazabicycloundecane, i.a.) is expediently added to the reaction solution in order to activate the 5-OH group and to neutralize any CF₃—SO₃H or CF₃—COOH which may have formed.

Hg cyanide or a combination of HgO with Hg chloride or Hg bromide, alternatively, may also be used in place of the silver salt (Helferich synthesis).

In a further variant, the reactivity of the sugar which is to be linked glycosidically in the 1'-position and whose other OH groups must be protected, may be increased by initial conversion into the 1'-phenylthio derivative and subsequent reaction with DAST (=diethylaminosulfur trifluoride) in absolutely dry dichloromethane (molecular sieve) at +5° C. to −30° C. to give the 1'-fluoro derivative. More reactive than the corresponding 1'-chloro- or 1'-bromo-derivative employed in the Koenigs-Knorr synthesis, the resulting 1'-fluoro-derivative of the sugar reactant may be linked to the 5-hydroxyl group of soraphen in the presence of SnCl₂ and AgClO₄ in a dry aprotic solvent, such as diethyl ether, under a protective gas, such as argon, at +5° C. to −30° C. (J. Am. Soc. 1984, 106, 4189-4192).

(B) Alternatively, it is possible to convert the protected monosaccharide to be activated in the 1'-position with 2,2'-dithiopyridine in dry dichloromethane at −10° C. to +10° C. under a protective gas atmosphere (for example argon) into the 1'-S-(2-pyridyl) monosaccharide, which reacts readily with the free 5-OH group of soraphen in the presence of Pb(ClO₄)₂ or AgClO₄ as the condensation agent at room temperature in tetrahydrofuran (THF) as the solvent, forming the glycosidic bond (J. Org. Chem. 1983, 48, 3489-3493).

(C) Alternatively, glycosidic links can be obtained in the presence of Lewis acids, such as AlCl₃, AlBr₃, SnCl₄, ZnCl₂, BF₃ (as well as especially the etherate), for which purpose acetylated sugars, in particular, are highly suitable (Chimia 21, 1967, p. 537-538).

(D) In the so-called ortho ester method, glycosidic bonds are alternatively obtained by reacting soraphen with the protected sugar to be linked in the presence of the ortho ester of a lower alcohol, whose one alcoholic component is the sugar reactant.

In the stricter sense, the process for the preparation of soraphen 5-glycosides of the formula I comprises a reaction of soraphen (a) with the sugar radical to be introduced and whose OH groups are protected, with the exception of the anomeric 1-OH group substituted in the 1-position by chlorine or bromine, with the exclusion of light in the temperature range of −30° C. to +60° C., preferably −5° C. to +30° C., and in the presence of a silver salt or mercury salt as the condensation agent; or (b) with the sugar radical to be introduced whose OH groups are protected, with the exception of the anomeric 1-OH group substituted in the 1-position by fluorine, with the exclusion of light at +5° C. to −30° C. and in the presence of SnCl₂ and AgClO₄ as the condensation agents; followed by mild hydrolysis of the hydroxyl protecting groups on the sugar radical.

As a rule, the protective groups can be detached by mild hydrolysis, for example with NH₃/methanol. Possible solvents in this part-step are, in particular, anhydrous aprotic representatives, such as dichloromethane, acetonitrile, benzene, toluene, nitromethane, dioxane, THF or ethylene glycol dimethyl ether; diethyl ether is particularly suitable.

Compounds of the formula I in which R₀ is a carbamoyloxy group —O—CO—N(R₄)(R₅) or a thiocarbamoyl group —O—CS—N(R₄)(R₅) may be obtained by carbamoylation of soraphen with (a) an isocyanate R₅—NCO or an isothiocyanate R₅—NCS in those cases in which R₄ is hydrogen, or with (b) a (thio)carbamic halide of the formula

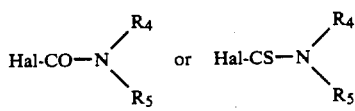

where R₄ and R₅ independently of one another have one of the indicated meanings and Hal is halogen, preferably chlorine or bromine.

In a further variant (c), the 5-hydroxyl group of soraphen can be converted with phosgene or thiophosgene in the presence of an acid-binding agent, such as pyridine, to give a chlorocarbonic ester or chlorothiocarbonic ester, respectively,

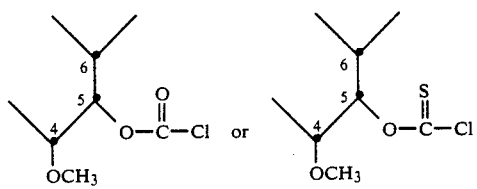

from which the desired carbamate

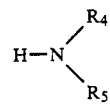

is obtained by reaction with a primary or secondary amine.

Suitable iso(thio)cyanates are, for example, trichloroacetyl isocyanate for introducing the unsubstituted carbamoyl group (—CO—NH₂), followed by mild removal under basic conditions of the CCl₃—CO radical, and then furthermore methyl isocyanate, trifluoromethyl isocyanate, tert-butyl isocyanate, chloroethyl isocyanate, allyl isocyanate, phenyl isocyanate, cyclopropyl isocyanate, cyclohexyl isocyanate, phenyl isothiocyanate, methyl isothiocyanate and isopropyl isothiocyanate.

Suitable examples of carbamoyl halides are dimethylcarbamoyl chloride, diethylcarbamoyl chloride, diisopropylcarbamoyl chloride, diphenylcarbamoyl chloride and di-sec-butylcarbamoyl chloride.

The carbamoylations with iso(thio)cyanates and carbamoyl halides are carried out in inert solvents free from hydroxyl groups, preferably in the presence of a tertiary amine, for example pyridine, 4-dimethylaminopyridine, lutidine, collidine, trialkylamine, N-dialkylaniline, or a bicyclic, non-nucleophilic base, for example 1,4-diazabicyclo[2.2.2]octane (DABCO), 1,5-diazabicyclo[4.3.0]non-5-ene (DBN) or 1,8-diazabicyclo[5.4.0]undec-7-ene (1,5-5) (DBU).

The reaction is generally carried out at temperatures from −10° C. to +150° C. when iso(thio)cyanates are employed, preferably 10° C. to 120° C., and preferably at +50° C. to 120° C. when carbamoyl halides are employed.

Unless the reaction is carried out using one of the abovementioned tertiary amines in excess, the following general solvents or solvent mixtures, for example, are recommended: aliphatic and aromatic hydrocarbons, such as benzene, toluene, xylenes, petroleum ether or hexane; halogenated hydrocarbons, such as chlorobenzene, methylene chloride, ethylene chloride, chloroform, carbon tetrachloride or tetrachloroethylene; ethers and ether-like compounds, such as dialkyl ethers (diethyl ether, diisopropyl ether, tert-butyl methyl ether etc.), anisole, dioxane or tetrahydrofuran; nitriles, such as acetonitrile or propionitrile; esters, such as ethyl acetate, propyl acetate or butyl acetate; ketones, such as acetone, diethyl ketone or methyl ethyl ketone; dimethyl sulfoxide (DMSO); dimethylformamide (DMF) and others. If mention is made thereof, these general solvents are also for the reactions which follow.

If it is desired to convert the 5-OH group in soraphen to the substituent $R_o$=halogen or azido, this is advantageously carried out via the step of the 5-sulfonic esters described further above. These esters can be converted with alkali metal halides or alkaline earth metal halides, or with alkali metal azides or alkaline earth metal azides, for example LiBr, KI, MgBr$_2$, KF or NaN$_3$, into the corresponding 5-halo compound or the 5-azido compound, respectively, in the temperature range from 0° to 170° C. in solvents such as acetone, lower alkanol, ethylene glycol or one of the abovementioned general solvents.

Thiol derivatives ($R_o$=—SH) can be obtained by reacting an appropriate sulfonic ester with a thio ester (for example potassium thioacetate) in a basic medium and a suitable solvent, such as acetone or one of the abovementioned general solvents. The thiocarboxylic ester which has formed can be cleaved under basic conditions (for example dilute alcoholic or aqueous hydroxide solution) at room temperature or under acid conditions (for example methanolic hydrochloric acid) at increased temperature.

5-Deoxy compounds ($R_o$=H) can be obtained starting from the appropriate thiols by reaction with Raney nickel in suitable solvents, such as alcohols, 1,4-dioxane etc. at temperatures from 10° to 100° C. They are also accessible by reacting soraphen with carbon disulfide (CS$_2$) in suitable solvents, for example acetone, ethers, etc., under basic conditions (for example KOH, NaH, etc.) at 0° C. to 50° C. The resulting xanthogenate can be alkylated for example using alkyl halides, for example methyl iodide, or alkyl sulfates (for example dimethyl sulfate) at 0° to 120° C. to give the corresponding xanthogenic esters. Examples of solvents which can be used are alcohols or one of the abovementioned general solvents. In a slightly better method, seraphen is converted with a halothioformic ester, such as phenyl chlorothioformate, in dry hydrocarbon or chlorohydrocarbon as the solvent in the presence of pyridine, to give the 5-O-thionocarbonate.

Therefrom and from the corresponding halides, the deoxy compound can be obtained by reaction with triaryltin hydrides or trialkyltin hydrides (for example tributyltin hydride) in inert solvents (for example benzene) in an inert gas atmosphere at temperatures between 0° C. and 120° C., with or without the use of free-radical starters, such as dibenzoyl peroxide, azobis-isobutyronitrile or exposure to light [Houben Weyl, "Methoden der organ. Chemie" (Methods of Organic Chemistry), Vol. 9, 1d, p. 341, 388 et seq.].

Etherification of the 5-OH group is carried out as such or in the alkali form or alkoxide form, using organic halides or sulfates. If the free OH group is present, the reaction is preferably carried out in the presence of acid-binding agents, such as alkali metal (hydrogen) carbonate or tertiary amines, such as trialkylamine or pyridine. Possible halides are preferably bromides and iodides, such as methyl iodide, propargyl bromide, allyl bromide, cyclopropyl bromide, cyclopentyl bromide, phenyl iodide or p-nitrophenyl bromide, but also chloromethyl methyl ether, advantageously in the presence of catalytic amounts of NaI. Lower alkyl groups can advantageously be introduced as alkyl sulfates, for example dimethyl sulfate, diethyl sulfate and others.

Examples of possible solvents are acetone, dimethylformamide, pyridine or ether-type compounds, such as tetrahydrofuran, diethyl ether or 1,2-dimethoxyethane. The reaction temperatures are at 0° to 100° C.

If interfering functional groups, such as OH, NH$_2$ or —COOH, are present in the molecule or in the reactant, these groups can be initially masked by acetylation or introduction of other protective groups, as already mentioned above [T. W. Green "Protective Groups in Organic Synthesis", J. Wiley & Sons, 1981 (New York)].

The enumeration of all abovementioned methods does not imply any limitation. If desired, the end products can be purified in a customary manner, for example by washing, digesting, extraction, recrystallization, chromatography etc.

The preparation processes which have been described, including all part-steps, form part of the present invention.

9,10-Dihydro-soraphen A can be obtained by hydrogenation from soraphen A or a derivative protected in the 5-position, for example using homogeneous hydrogenation catalysts on a transition metal complex basis (for example rhodium or iridium complexes).

It must be pointed out that the macrocyclic soraphens of the formula I are usually present in the hemiacetal form which has been indicated, but that this form can undergo reversible ring opening according to the diagram

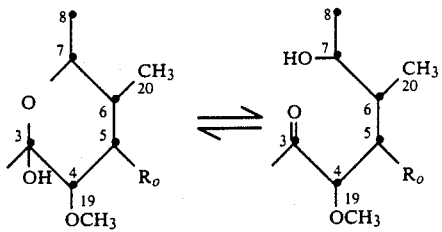

Depending on the preparation or working-up technique, the soraphens are obtained in one or the other form or as a mixture of both forms, depending on the pH and on the solvent. The shift of the $^{13}$C-NMR signal in the 3-position and that of the $^1$H-NMR signals in certain other positions is typical of the ring opening. In the case of soraphen A, for example, the following modifications are observed: $^{13}$C-NMR(CDCl$_3$, δ in ppm) 99.5→203.1(3-C).$^1$H-NMR(CDCl$_3$, δ in ppm): 3.14→3.72(2-H); 3.18→4.5(4-H); 3.83→3.16 (7-H); 5.86→5.7 (17-H). Similar shifts are also observed in the soraphen derivatives of the formula I mentioned herein. In principle, the formula I of the present invention embraces the 3-hemiacetal form, which is preferred in the lower pH range, and the opened 3-keto-7-hydroxy form, as well as all possible stereoisomers which come under the formula I.

It has been found that compounds of the formula I have a biocidal spectrum against phytopathogenic microorganisms, in particular against fungi, which is highly favourable for practical requirements. They have highly advantageous curative, systemic and in particular preventive properties and are employed for the protection of numerous crop plants. Using the active substances of the formula I, pests which occur on plants or parts of plants (fruits, flowers, foliage, stalks, tubers, roots) of various crops can be brought under control or destroyed, additional growth of parts of plants which occurs later also being kept free from phytopathogenic microorganisms.

As microbicides, the active substances of the formula I are active for example against the phytopathogenic fungi belonging to the following classes: Fungi imperfecti (for example in particular Botyritis, furthermore Pyricularia, Helminthosporium, Fusarium, Septoria, Cercospora and Alternaria); Basidiomycetes (for example Rhizoctonia, Hemileia, Puccinia). Moreover, they are active against the class of the Ascomycetes (for example in particular Venturia and Erysiphe, furthermore Podosphaera, Monilinia, Uncinula) and of the Oomycetes (for example Phytophthora, Plasmopara). The compounds of the formula I can furthermore be employed as seed-dressing agents for treating of seeds (fruits, tubers, grains) and of cuttings in order to protect them from fungal infections, as well as phytopathogenic fungi.

The invention also relates to the agents which contain compounds of the formula I in one of the possible stereoisomeric forms as the active ingredient, in particular plant-protecting agents, as well as the use thereof in the agricultural sector or in related fields.

This also applies to a process for the treatment of plants which is distinguished by the application of the novel compounds of the formula I or of the corresponding novel agents.

Examples of target crops for the plant protection use disclosed in this publication within the scope of this invention, are the following plant species: cereals (wheat, barley, rye, oats, rice, maize, sorghum and related species); beet (sugar beet and fodder beet); pomaceous fruit, stone fruit and stone fruit (apples, pears, plums, peaches, almonds, cherries, strawberries, raspberries and blackberries; pulses (beans, lentils, peas, soya beans); oil crops (oil seed rape, mustard, poppy, olives, sunflowers, coconuts, castor, cocoa, peanuts); the gourd family (pumpkin, cucumbers, melons); fibre plants (cotton, flax, hemp, jute); citrus fruit (oranges, lemons, grapefruit, tangerines); various vegetables (spinach, lettuce, asparagus, cabbage species, carrots, onions, tomatoes, potatoes, paprika); the Lauraceae (avocado, cinnamomum, camphor) or plants such as tobacco, nuts, coffee, pineapple, sugar cane, tea, pepper, vines, hops, the banana family and plants which yield natural rubber, as well as ornamental plants (Compositae). This enumeration does not represent any limitation.

Active substances of the formula I are customarily used in the form of compositions and can be applied to the area or plant to be treated either simultaneously or in succession with other active substances. These other active substances can be fertilizers, suppliers of trace elements or other preparations which influence plant growth. In this context, it is also possible to use selective herbicides as well as insecticides, fungicides, bactericides, nematicides, molluscicides or mixtures of a plurality of these preparations, if desired together with further carriers conventionally used in the art of formulation, surfactants or other additives which assist application.

Suitable carriers and additives can be solid or liquid and correspond to the substances advantageously used in the art of formulation, for example natural or regenerated mineral substances, solvents, dispersants, wetting agents, tackifiers, thickeners, binders or fertilizers.

A preferred method of applying an active substance of the formula I or an agrochemical agent which contains at least one of these active substances, is application onto the foliage (leaf application). In this context, the frequency of application and the dosage rate depend on the infection pressure of the specific pathogen. However, the active substances of the formula I can also enter the plant via the soil and the root system (systemic action), by drenching the site where the plant grows with a liquid preparation, or by incorporating the substances in solid form into the soil, for example in the form of granules (soil application).

Compounds of the formula I can also be applied to seeds (coating), either by immersing the grains in a liquid preparation of the active substance or by coating them with a solid preparation.

In this context, the compounds of the formula I are employed in unaltered form or, preferably, together with the adjuvants conventionally used in the art of formulation. For this purpose, they are expediently processed in a known manner, for example to give emulsion concentrates, spreadable pastes, directly sprayable or dilutable solutions, dilute emulsions, wettable powders, soluble powders, dusts, granules or encapsulations, for example in polymeric substances. The application methods, such as spraying, misting, dusting, scattering, brushing or watering, as well as the type of the agents, are chosen to suit the intended use and the circumstances which prevail. Advantageous application rates are generally at around 10 g to 500 g of active substance (a.s.) per hectare, preferably at around 50 g to 500 g of a.s./ha.

The preparations, i.e. the agents containing the active substance of the formula I and a solid or liquid additive, are prepared in a known manner.

Possible solvents are: aromatic and aliphatic hydrocarbons, for example xylene mixtures, cyclohexane or paraffins; also alcohols and glycols as well as their ethers and esters, such as ethanol, ethylene glycol, ethylene glycol monomethyl ether or ethylene glycol monoethyl ether, or acetic esters; ketones, such as cyclohexanone, strongly polar solvents, such as N-methyl-2-pyrrolidone, dimethyl sulfoxide or dimethylformamide, as well as epoxidized and unepoxidized vegetable oils, such as epoxidized coconut oil or soya oil; or water.

Solid carriers which are generally used, for example for dusting agents and dispersible powders, are ground natural minerals, such as calcite, talc, kaolin, montmorillonite or attapulgite. To improve the physical properties, it is also possible to add highly-disperse silicic acid or highly-disperse absorptive polymers. Possible adsorptive, granulated granule carriers are porous types, for example pumice, ground brick, sepiolite or bentonite, possible non-sorptive carriers are, for example, calcite or sand. In addition, a large range of pregranulated materials of inorganic nature, such as, in particular, dolomite, or comminuted plant residues, can be used.

Suitable surface-active compounds are non-ionogenic or cation-active and/or anion-active surfactants having good emulsifying, dispersing and wetting properties, depending on the type of the active substance of the formula I to be formulated. Surfactants are also understood as meaning mixtures of surfactants.

Suitable anionic surfactants can be either so-called water-soluble soaps or water-soluble synthetic surface-active compounds.

More frequently, however, so-called synthetic surfactants are used, in particular alkanesulfonates, fatty alcohol sulfates, sulfonated benzimidazole derivatives or alkylsulfonates.

Possible non-ionic surfactants are polyglycol ether derivatives of aliphatic or cycloaliphatic alcohols, of saturated or unsaturated fatty acids and of alkylphenols, which can contain 3 to 30 glycol ether groups and 8 to 20 carbon atoms in the (aliphatic) hydrocarbon moiety and 6 to 18 carbon atoms in the alkyl moiety of the alkylphenols.

Further examples of non-ionic surfactants which may be mentioned are nonylphenol polyethoxyethanols, castor oil polyglycol ethers, polypropylene/polyethylene oxide adducts, tributylphenoxypolyethyleneethanol, polyethylene glycol and octylphenoxypolyethoxyethanol.

Further suitable substances are also fatty acid esters of polyoxyethylene sorbitan, such as polyoxyethylene sorbitan trioleate.

Further surfactants which are used in the art of formulation are known to those skilled in the art or can be found in the specialized literature.

As a rule, the agrochemical preparations contain 0.1 to 95% of active substance of the formula I, 99.9 to 5% of a solid or liquid additive and 0 to 25% of a surfactant.

While fairly concentrated agents are preferred as commercial goods, the end consumer, as a rule, uses dilute agents.

The agents can also contain further additives, such as stabilizers, defoamers, viscosity regulators, binders, tackifiers as well as fertilizers or other active substances, for obtaining specific effects.

The examples which follow are intended to illustrate the invention in greater detail without imposing any limitation. (The symbols denote: h=hour, PLC=preparative layer chromatography, TLC=thin-layer chromatography, RT=room temperature).

1. PREPARATION EXAMPLES

H-1. Preparation of soraphen A 5-formate (Compound No. 1)

50.0 mg (0.096 mmol) of soraphen A and 11.7 mg (0.096 mmol) of 4-dimethylaminopyridine (DMAP) are dissolved in 2 ml of dry dichloromethane, and the solution is treated with 8.7 μl (10.7 mg, 0.233 mmol) of formic acid and 66.6 μl (48.4 mg, 0.478 mmol) of triethylamine. The reaction mixture is cooled to 10° C. and treated with 18.5 μl (20.0 mg, 0.196 mmol) of acetic anhydride and stirred for 30 minutes. The ice-bath is removed, and stirring is continued for 30 minutes at room temperature. The reaction mixture is then treated with a few drops of methanol and concentrated. The residue is treated with water and extracted several times using ethyl acetate. The combined organic phases are washed in succession with 1N HCl (pH 0), 5% sodium hydrogen carbonate solution (pH 8) and with a concentrated solution of sodium chloride (pH 6). The mixture is then dried over sodium sulfate and concentrated on a rotary evaporator. This gives 50.7 mg (0.092 mmol, 96%) of the NMR-spectroscopically uniform product.

H-2. Preparation of soraphen A 5-propionate (Compound No. 6)

50 mg (0.096 mmol) of soraphen A are dissolved in 0.5 ml of dry pyridine, and the solution is treated with 28 μl (29.6 mg, 0.320 mmol) of propionyl chloride as well as 12 mg (0.10 mmol) of DMAP. The solution is stirred for 20 hours at room temperature and then substantially concentrated, treated with water and extracted with ethyl acetate. The combined organic phases are washed using 5% NaHCO$_3$ solution and saturated solution of sodium chloride, dried over sodium sulfate and concentrated on a rotary evaporator. This gives 53 mg of a crude product which is purified by means of PLC (Merck, silica gel 60, mobile phase: dichloromethane/acetone 90:10).

This gives 23 mg (0.040 mmol, 42%) of the product.

H-3. Preparation of Soraphen A 5-carbamate (Compound No. 139)

30 mg (0.06 mmol) of soraphen A are dissolved in 0.5 ml of dry dichloromethane, and the solution is treated with 14 μl (22 mg, 0.12 mmol) of trichloroacetyl isocyanate. After 10 minutes, the reaction mixture is filtered over neutral aluminium oxide, which removes the trichloroacetyl group, and diluted with dichloromethane.

This gives 32.0 mg of the crude product which is purified by means of PLC (silica gel 60F$_{254}$, mobile phase: dichloromethane/methanol/toluene 94:5:1). Yield: 29.0 mg (0.05 mmol, 83%) of a white solid.

H-4. Preparation of 5-methoxy-soraphen A (Compound No. 92)

16 mg (0.03 mmol) of soraphen A are dissolved in 0.5 ml of dimethyl sulfoxide (DMSO), and the solution is treated with 10 mg (0.18 mmol) of KOH, as well as 50 μl (104 mg, 0.80 mmol) of CH$_3$Cl. The reaction mixture is stirred for 5 hours at room temperature and then substantially concentrated. The residue is treated with a buffer solution (pH 7) and extracted with ethyl acetate. The organic phase is washed with concentrated NaCl solution, dried over Na$_2$SO$_4$ and concentrated on a rotary evaporator. This gives 12 mg of the crude product which is purified by means of PLC (silica gel 60, mobile phase: CH$_2$Cl$_2$/acetone 90:10). The unpolar zone is eluted. Yield: 4.5 mg (0.008 mmol, 26%) of a colourless oil.

H-5. Preparation of soraphen A 5-mesylate (Compound No. 74)

102 mg (0.195 mmol) of soraphen A are dissolved in 5 ml of dry dichloromethane, the solution is treated in succession with 67 μl (49 mg, 0.484 mmol) of Et$_3$N and 19 μl (28 mg, 0.244 mmol) of mesyl chloride, and stirred for 1 hour at room temperature. The reaction mixture is then treated with 1N HCl and extracted with CH$_2$Cl$_2$. The combined organic phases are washed with 5% NaHCO$_3$ solution and concentrated NaCl solution, dried over CaCl$_2$ and concentrated on a rotary evaporator.

This gives 116 mg (0.193 mmol, 99%) of the NMR spectroscopically uniform crude product which can be purified by means of PLC (Merck, silica gel 60, mobile phase: CH$_2$Cl$_2$/acetone 90:10) for characterization.

H-6. Preparation of 5-tert-butyldimethylsilyloxy-soraphen A (Compound No. 73)

20 mg (0.038 mmol) of soraphen A are dissolved in 1 ml of dimethylformamide (DMF), and the solution is treated with about 50 mg (0.33 mmol) of imidazole, about 50 mg (3.40 mmol) of t-butyldimethylsilyl chloride and 5 mg (0.04 mmol) of DMAP. The mixture is stirred for 2 days at room temperature, and the reaction mixture is then substantially concentrated. The residue is treated with buffer solution (pH 7) and extracted with ethyl acetate. The organic phase is washed with concentrated NaCl solution, dried over Na$_2$SO$_4$ and concentrated on a rotary evaporator. This gives 25.5 mg of the crude product which is purified by means of preparative medium-pressure chromatography (stationary phase: Lichroprep Si 60, 25–40 μm, Merck Catalogue No. 9390; mobile phase: CH$_2$Cl$_2$/t-butyl methyl ether 96:4, flow rate 26 ml/min, pressure: 12 bar). This gives 10 mg (0.016 mmol, 42%) of a colourless oil.

H-7. Preparation of soraphen B 5,11-diacetate (Compound No. 10)

29 mg (0.057 mmol) of soraphen B are dissolved in 0.5 ml of pyridine, and the solution is treated with 46 μl (50 mg, 0.49 mmol) of acetic anhydride. The reaction mixture is stirred overnight at room temperature and then concentrated substantially. The residue is treated with water and extracted with ethyl acetate. The combined organic phases are subsequently washed with 1N HCl, 5% NaHCO$_3$ solution and saturated NaCl solution, dried over NaSO$_4$ solution and concentrated on a rotary evaporator. This gives 28 mg of the crude product which is purified by means of PLC (silica gel 60, mobile phase: CH$_2$Cl$_2$/acetone 93:7, elution of the unpolar zone). Yield: 12 mg (0.020 mmol, 35%) of a colourless oil.

H-8. Preparation of soraphen B 5-acetate (Compound No. 12) and soraphen B 11-acetate (Compound No. 165)

18 mg (0.035 mmol) of soraphen B are dissolved in 0.1 ml of pyridine, and the solution is treated with 30 μl (32 mg, 0.32 mmol) of acetic anhydride. The reaction mixture is stirred for 3 hours at room temperature and then substantially concentrated, treated with 1N HCl and extracted with ethyl acetate. The combined organic phases are washed with concentrated NaCl solution, dried over Na$_2$SO$_4$ and concentrated on a rotary evaporator. The crude product is purified by means of PLC (Merck, silica gel 60, mobile phase: CH$_2$Cl$_2$/acetone 90:10).

H-9. Preparation of soraphen A 5-t-butyl carbonate (Compound No. 170)

50 mg (0.1 mmol) of soraphen A are dissolved in 1 ml of dichloromethane, and the solution is treated with 70 μl (51 mg, 0.23 mmol) of triethylamine. To this solution, cooled to −10° C., there are added 44 mg (0.20 mmol) of di-t-butyl pyrocarbonate. After the mixture has been stirred for 2 hours at −10° C., the reaction is complete. The mixture is treated with 1N HCl and extracted with ethyl acetate. The combined organic phases are washed with 5% NaHCO$_3$ solution and saturated solution of sodium chloride, dried over sodium sulfate and concentrated on a rotary evaporator. This gives 45 mg of the crude product which is purified by means of PLC (Merck, silica gel 60, mobile phase: dichloromethane/acetone 95:5).

This gives 26 mg (0.042 mmol, 40%) of the product.

H-10. Preparation of 5-O-tetrahydropyranyl-soraphen A as isomer I and as isomer II (Compound No. 131)

200 mg (0.38 mmol) of soraphen A, dissolved in 5 ml of dichloromethane, are treated with 180 μl (166 mg, 1.97 mmol) of 3,4-dihydro-2H-pyrane and 1 mg of p-toluenesulfonic acid hydrate. After the reaction solution has been stirred for 15 minutes at room temperature, it is treated with 5% NaHCO$_3$ solution and extracted twice with ethyl acetate. The combined organic phases are washed with saturated NaCl solution, dried over Na$_2$SO$_4$ and concentrated on a rotary evaporator.

This gives 215 mg (90%) of the 5-O-THP ether as 1:1 isomer mixture. The isomers can be separated by means of MPLC (Merck Lichroprep Si 60, 15–25 μm, Cat. No. 9336, mobile phase: dichloromethane/methanol, 995:5, detection at 254 nm). Isomer I elutes first, followed by isomer II.

TABLE 1

| No. | $R_f$(mob. ph.)* | MS(EI) M$^+$ | 2-H | 4-H | 5-H | 6-H | 8-H | 3-OH | R/R$_o$ |
|---|---|---|---|---|---|---|---|---|---|
| 1 | 0.68 (1) | 548 | 3.14 | 3.14 | 5.29 | 1.88 | 2.45 | 3.92 | 8.12 (s, 1H) |
| 4 | 0.58 (1) | 562 | 3.12 | 3.10 | 5.05 | 1.82 | 2.45 | 3.74 | 2.12 (s, 3H) |
| 5 | — | 616 | 3.12 | 3.21 | 5.12 | 1.94 | 2.46 | 3.72 | — |
| 6 | 0.73 (1) | 576 | 3.14 | 3.10 | 5.06 | 1.82 | 1.96 | 3.72 | 1.16 (t, 3H), 2.39 (q, 2H) |
| 7 | 0.63 (1) | 590 | 3.11 | 3.09 | 5.06 | 1.82 | 2.45 | 3.72 | 0.98 (t, 3H), 1.67 (m, 2H), 2.35 (t, 2H) |
| 8 | 0.46 (2) | 590 | 3.12 | 3.08 | 5.03 | 1.82 | 2.46 | 3.70 | 1.19 (d, 3H), 1.20 (d, 3H), 2.60 (qq, 1H) |
| 15 | 0.51 (2) | 624 | 3.18 | 3.26 | 5.30 | 2.02 | 2.52 | 3.81 | 7.48 (pt, 2H), 7.59 (pt, 1H), 8.08 (pd, 2H) |
| 139 | 0.55 (3) | 563 | 3.13 | 3.15 | 4.96 | 1.87 | 2.45 | 3.82 | 6.52 (s, b), 6.67 (s, b), NH$_2$ |
| 141 | 0.31 (2) | 639 | 3.15 | 3.22 | 5.07 | 1.93 | 2.47 | 3.80 | 6.77 (b, N—H), 7.07 (m, 1H), 7.32 (m, 2H), 7.43 (m, 2H) |
| 67 | — | 592 | 3.03 | 2.96 | 4.11 | 1.64 | 2.50 | 5.29 | 0.18 (s, 9H) |
| 92 | 0.61 (1) | 534 | 3.04 | 3.11 | 3.60 | 1.97 | 2.50 | 4.89 | 3.43 (s, 3H) |
| 74 | 0.63 (1) | 598 | 3.15 | 3.34 | 4.91 | 2.08 | 2.45 | 3.80 | 3.11 (s, 3H) |
| 75 | 0.61 (1) | — | 3.06 | 3.15 | 4.67 | 1.83 | 2.35 | 3.78 | 2.46 (s, 3H), 7.37 (pd, 2H), 7.84 (pd, 2H) |
| 73 | 0.68 (1) | 634 | 3.02 | 2.98 | 4.14 | 1.74 | 2.51 | 5.17 | 0.14 (s, 3H), 0.15 (s, 3H), 0.92 (s, 9H) |
| 25 | 0.81 (1) | — | 3.13 | 3.23 | 5.09 | 1.99 | 2.46 | 3.70 | — |
| 12 | 0.37 (1) | — | 3.10 | 3.07 | 5.04 | ** | ** | 3.84 | 2.13 (s, 3H) |
| 10 | 0.45 (2) | — | 3.11 | 3.06 | 5.04 | ** | ** | 3.91 | 2.08 (s, 3H), 2.13 (s, 3H) |
| 13 | 0.35 (1) | 578 | 3.10 | 3.05 | 5.06 | ** | ** | 3.83 | 0.98 (t, 3H), 1.69 (m, 2H), 2.36 (t, 2H) |
| 11 | — | 648 | 3.11 | 3.06 | 5.04 | ** | 2.12 | 3.89 | 5.06 (H-11), 2.34 (m, 4H) |
| 14 | 0.39 (1) | 612 | 3.16 | 3.21 | 5.29 | ** | 2.17 | 3.92 | 7.49 (pt, 2H), 7.59 (pt, 1H), 8.09 (pd, 2H) |
| 165 | 0.46 (1) | — | 3.09 | 3.14 | 3.97 | ** | ** | 4.46 | 2.08 (s, 3H), 5.08 (m, 1H) |
| 170 | 0.66 (1) | 620 | 3.12 | 3.14 | 4.88 | 1.89 | 2.47 | 3.88 | 1.52 (s, 9H) |

TABLE 1-continued

| No. | $R_f$(mob. ph.)* | MS(EI) M+ | 1H-NMR-Data of selected signals (CDCl$_3$, δ in ppm) | | | | | | |
|---|---|---|---|---|---|---|---|---|---|
| | | | 2-H | 4-H | 5-H | 6-H | 8-H | 3-OH | R/R$_o$ |
| 149 | 0.56 (1) | 578 | 3.14 | 3.18 | 4.91 | 1.97 | 2.47 | 3.90 | 3.82 (s, 3H) |
| 22 | 0.69 (1) | 692 | 3.19 | 3.25 | 5.32 | 2.00 | 2.51 | 3.85 | 7.74 (m, 2H), 8.20 (m, 2H) |
| 171 | 0.49 (2) | 604 | 3.12 | 3.08 | 5.00 | 1.79 | 2.47 | 3.67 | 1.22 (s, 9H) |
| 55 | 0.32 (4) | | 3.12 | 3.11 | 5.05 | 1.84 | 2.44 | — | 2.64 (m, 4H) |
| 49 | 0.64 (1) | 602 | 3.14 | 3.13 | 5.11 | 1.88 | 2.47 | 3.77 | 6.91 (m, 1H) |
| 32 | 0.57 (1) | 574 | 3.14 | 3.15 | 5.14 | 1.88 | 2.47 | 3.76 | 5.88 (m, 1H), 6.20 (m, 1H), 6.47 (m, 1H) |
| 47 | 0.36 (1) | 592 | 3.15 | 3.12 | 5.12 | 1.86 | 2.45 | 3.71 | 4.08 (m, 2H) |
| 50 | 0.39 (1) | | 3.10 | 3.09 | 5.09 | ** | 2.12 | 3.92 | 4.05 (m, 2H), 4.10 (2H), 5.17 (m, 2H) |
| 131 | 0.44 (1) | 604 | 3.07 | 3.18 | 4.17 | 1.96 | 2.51 | 4.85 | 1.57 (m, 4H), 1.77 (m, 2H), 3.56 (m, 1H) 3.86 (m, 1H), 4.70 (m, 1H) |
| 131 | 0.42 (1) | 604 | 3.06 | 3.02 | 4.07 | 1.99 | 2.51 | 4.82 | 1.62 (m, 4H), 1.75 (m, 2H), 3.55 (m, 1H), 3.81 (m, 1H), 4.69 (m, 1H) |
| 168 | 0.33 (1) | | 3.09 | 3.12 | 3.98 | 1.86 | 2.18 | — | 4.05 (m, 2H), 5.20 (m, 1H, 11-H), 3.81 (m, 1H), 4.69 (m, 1H) |

*Mobile phase 1: dichlormethane/acetone 90:10
Mobile phase 2: dichlormethane/acetone 95:5
Mobile phase 3: dichlormethane/acetone 75:25
Mobile phase 4: dichlormethane/acetone/methanol 78:20:2
**Signal masked

TABLE 2

| No. | 13C-NMR-Datea of selected signals (CDCl$_3$, δ in ppm) | | |
|---|---|---|---|
| | Carbonyl-C | C-4/C-5/C-7/C-17 | R/R$_o$ |
| 1 | 160.2/170.8 | 70.0/72.4/74.5/74.8* | — |
| 4 | 170.4/171.0 | 70.4/72.4/74.1/74.7* | 21.5 |
| 5 | 170.8/— | 71.9/73.4/74.5/74.7* | — |
| 6 | 171.0/173.9 | 70.3/72.5/74.1/74.8* | 9.0, 35.9 |
| 7 | 171.0/173.0 | 70.3/72.6/74.2/74.9* | 13.7, 35.9, 36.5 |
| 8 | 171.1/176.5 | 70.1/72.5/74.1/74.6* | 18.8, 18.9, 34.0 |
| 15 | 166.0/171.1 | 70.7/72.7/74.5/74.9* | 129.8, 130.4, 133.2 |
| 139 | 155.9/171.0 | 71.0/72.6/74.2/75.0* | — |
| 141 | 152.8/171.0 | 71.0/72.7/74.3/75.9* | 118.7, 123.6, 129.1, 137.7 |
| 67 | — | — | — |
| 92 | 171.1/— | 72.2/72.5/74.4/79.1* | 57.7 |
| 74 | 170.7/— | 71.8/74.6/75.2/76.3* | 39.1 |
| 75 | 170.9/— | 71.6/74.5/75.4/77.5* | 21.7, 127.9, 129.9, 134.7, 145.1 |
| 73 | 171.2/— | 70.8/71.8/72.0/77.3* | 5.0, 25.9 |
| 25 | 161.5/170.9 | 72.1/74.0/74.6/75.6* | 89.9 |
| 170 | 153.0/171.1 | 72.1/73.2/73.9/75.1* | 27.9, 82.9 |
| 149 | 155.2/171.0 | 72.1/74.1/74.4/74.8* | 54.9 |
| 22 | 164.8/170.9 | 71.2/72.7/74.7/74.9* | 125.5, 125.6, 130.3, 133.7 |
| 171 | 171.2/177.9 | 70.0/72.6/74.2/74.6* | 27.1, 38.9 |
| 55 | 170.9/171.9 | 70.8/72.8/74.0/74.9* | 32.3, 35.1 |
| 49 | 167.3/171.2 | 70.2/72.7/74.2/74.9* | 12.1, 14.6, 138.2 |
| 32 | 165.6/171.1 | 70.5/72.5/74.3/74.8* | 128.5, 131.6 |
| 47 | 169.8/170.9 | 70.9/72.4/74.3/74.6* | 69.9 |
| 50 | 169.9/170.1/171.6 | 69.8/71.2/74.7/76.1* | 57.7, 59.4, 69.9 |
| 131 | 171.2 | 72.1/72.1/73.2/77.3* | 19.6, 25.2, 31.2, 63.2, 97.7 |
| 131 | 171.1 | 72.3/72.5/74.5/75.1* | 19.3, 25.2, 31.1, 62.9, 98.8 |

*unassigned

H-11. Preparation of 5-O-(2,4-dinitrophenyl)-soraphen A (Compound No. 172)

25 mg (0.1 mmol) of soraphen A and 30 mg of 2,4-dinitro-1-fluorobenzene (2 equivalents) are dissolved in 1 ml of dry DMF, and the solution is sprayed to 8 mg of sodium hydride. After the mixture has been stirred for 78 hours at RT, a thin-layer chromatogram (TLC) shows that the reaction is complete (mobile phase: dichloromethane/acetone, 9:1, v/v; educt $R_f$ 0.3, product $R_f$ 0.6).

The solution is diluted with 10 ml of 1N hydrochloric acid (=HCl) and extracted twice with ethyl acetate, the solvent is distilled off, and the product is purified with the aid of PLC (silica gel Si 60, 1 mm, mobile phase: dichloromethane/acetone, 9:1, v/v; $R_f$ 0.5). Yield: 23 g=34% of theory.

1H-NMR (CDCl$_3$): δ=2.12 (m, 1H, H-6); 2.50 (m, 1H, H-8); 3.09 (q, 1H, H-2); 3.24 (d, 1H, H-4); 4.35 (s, 1H, 3-OH); 4.87 (m, 1H, H-5); 7.27, 8.47, 8.86 (2,4-dinitrophenyl).

13C-NMR (CDCl$_3$): δ=31.90 d, 35.09 d (C-6, C-8); 98.34 s (C-3); 170.75 s (C-1); 115.06 d, 122.86 d, 129.26 d, 139.80 s, 140.65 s, 154.95 s (2,4-dinitrophenyl).

IR (film): υ=3544, 2933, 2885, 2829, 1731, 1608, 1538, 1488, 1483, 1347, 1276, 1149, 1093, 977, 836, 745, 701 cm$^{-1}$.

UV (methanol): $\lambda_{max}$ (1 g ε)=289 nm (4.11)

MS (70 eV): m/e (%) =686 (0.4, M+), 654 (0.3), 497 (2), 479 (1), 465 (1), 297 (1), 281 (2), 189 (25), 157 (94), 91 (100)

Analysis. $C_{35}H_{46}N_2O_{12}$: Calculated: 686.3050. Found: 686.3065 M+.

H-12. Preparation of 5-O-allyl-soraphen A (Compound No. 84)

52 mg (0.1 mmol) of soraphen A and 60 mg of allyl bromide (5 equivalents) are dissolved in 0.7 ml of dry DMF, and the solution is sprayed to 22 mg (2 equivalents) of potassium tert-butylate. After the mixture has been stirred for 15 minutes at room temperature, TLC (mobile phase: dichloromethane/acetone, 9:1, v/v;

educt R/0.3, product R/0.6) shows that the reaction is complete.

The solution is diluted with 10 ml of 1N HCl and extracted twice with ethyl acetate, the solvent is distilled off, and the product is purified with the aid of TLC (silica gel Si 60, 1 mm, mobile phase: dichloromethane/acetone, 9:1, v/v; R/0.5). Yield: 14.8 mg=27% of theory.

$^1$H-NMR (CDCl$_3$): δ=1.92 (m, 1H, H-6); 2.50 (m, 1H, H-8); 3.03 (q, 1H, H-2); 3.10 (d, 1H, H-4); 3.78 (m, 1H, H-5); 4.97 (s, 3-OH); 4.02, 4.14, 5.24, 5.30, 5.89 (allyl).

$^{13}$C-NMR (CDCl$_3$): δ=31.67 d, 35.23 d (C-6, C-8); 99.07 s (C-3); 171.07 s (C-1); 71.16 t, 118.08 t, 133.97 d (allyl).

IR (film): υ=3487, 2960, 2933, 2871, 1733, 1463, 1380, 1260, 1177, 1096, 1071, 990, 747 cm$^{-1}$ UV (methanol): λ$_{max}$ (1 g ε)=204 nm (4.09)

MS (70 eV): m/e (%)=560 (5, M+), 542 (3), 528 (2), 502 (2), 470 (4), 295 (5), 215 (10), 189 (32), 157 (94), 71 (100).

Analysis. C$_{32}$H$_{48}$O$_8$: Calculated: 560.3369. Found: 560.3352 M+.

H-13. Preparation of the 5-O-glycine ester of soraphen A (Compound No. 53)

(a) Preparation of the intermediate N-(BOC)-glycine ester 52 mg (0.1 mmol) soraphen A, 19 mg of N-tert-butyloxycarbonyl-glycine (=N-BOC-glycine) (1.1 equivalents), 26 mg of dicyclohexylcarbodiimide (=DCC) (1.2 equivalents) and 1.2 mg of N,N-dimethylaminopyridine (=DMAP) are dissolved in 1 ml of dry dichloromethane, and the solution is stirred for 1 hour at RT. A TLC (dichloromethane/acetone, 9:1, v/v; educt R/0.3, product R/0.5) shows that the reaction is complete.

The solution is filtered and concentrated, and the product is purified with the aid of PLC (silica gel Si 60, 1 mm, mobile phase: dichloromethane/acetone, 9:1, v/v; R/0.4).

Yield: 48.0 mg=71% of theory.

$^1$H-NMR (CDCl$_3$): δ=1.85 (m, 1H, H-6); 2.45 (m, 1H, H-8); 3.10 (q, 1H, H-2); 3.11 (d, 1H, H-4); 3.74 (s, 3-OH); 5.08 (d, 1H, H-5); 1.46 (s, 9 H, BOC); 3.95 (d, 2 H, glycine).

IR (film): υ=3539, 3402, 2975, 2935, 2829, 1750, 1723, 1519, 1461, 1370, 1230, 1168, 1093, 987, 701 cm$^{-1}$.

UV (methanol): λ$_{max}$ (1 g ε)=207 nm (3.42)

MS (70 eV): m/e (%)=677 (1, M+), 659 (1), 645 (1), 502 (1), 470 (3), 414 (3), 296 (7), 157 (98), 91 (96), 57 (100).

Analysis. C$_{36}$H$_{55}$NO$_{11}$: Calculated: 677.3775. Found: 677.3788 (M-1)+.

(b) Preparation of the end product 50 mg (75 μmol) of the 5-soraphenyl (N-BOC)-glycine ester obtained in (a) are dissolved in 1 ml of THF and the solution is treated with 1 ml of 6N HCl and stirred for 2 hours at RT. A TLC (mobile phase: dichloromethane/methanol, 9:1, v/v; educt R/0.8, product R/0.4) shows that the reaction is complete. The solution is neutralized to pH 7 using sodium hydrogen carbonate solution and extracted five times with ethyl acetate, and the extract is concentrated. The crude product is purified with the aid of PLC (silica gel Si 60, 1 mm, mobile phase: dichloromethane/methanol, 9:1, v/v; R/0.2). Yield: 35.0 mg=76% (as the hydrochloride)

$^1$H-NMR (CDCl$_3$): δ=1.83 (m, 1H, H-6); 2.44 (m, 1H, H-8); 3.10 q, 1H, H-2); 3.11 (d, 1H, H-4); 5.06 (d, 1H, H-5); 3.26 (s, 2H, glycine).

$^{13}$C-NMR (CDCl$_3$): δ=32.52 d, 35.25 d (C-6, C-8); 98.43 s (C-3); 170.97 s (C-1); 44.11 t, 173.34 s (glycine).

IR (film): υ=3368, 2931, 2861, 2827, 1727, 1708, 1481, 1380, 1253, 1189, 1152, 1100, 1069, 992, 975, 738, 699 cm$^{-1}$.

UV (methanol): λ$_{max}$ (1 g ε)=205 nm (4.15)

MS (70 eV): m/e (%)=577 [1(M-H)+], 599 (1), 545 (5), 527 (3), 513 (2), 502 (1), 484 (1), 470 (3), 290 (10), 232 (9), 189 (34), 157 (100).

H-14. Preparation of the 5-O-phenylthionocarbonate of soraphen A (Compound No. 173)

52 mg (0.1 mmol) of soraphen A and 32 mg of pyridine (4 equivalents) are dissolved in 1 ml of dry dichloromethane, and the solution is treated with 35 mg O-phenyl chlorothioformate (2 equivalents). After 4 days, a TLC (dichloromethane/ether, 4:1, v/v; educt R/0.25, product R/0.65) shows that the reaction is almost complete.

The solution is concentrated, and the product is purified with the aid of PLC (silica gel Si 60, 1 mm, mobile phase: dichloromethane/ether, 4:1, v/v; R/0.5). Yield: 45.7 mg=70%

$^1$H-NMR (CDCl$_3$): δ=2.08 (m, 1H, H-6); 2.48 (m, 1H, H-8); 3.17 (q, 1H, H-2); 3.37 (d, 1H, H-4); 3.84 (s, 3-OH); 5.56 (d, 1H, H-5); 7.16, 7.27, 7.42 (phenylthionocarbonate).

$^{13}$C-NMR (CDCl$_3$): δ=32.36 d, 35.26 d (C-6, C-8); 98.27 s (C-3); 170.98 s (C-1); 122.05 d, 126.67 d, 129.50 d, 153.36 s (phenylthionocarbonate).

IR (film): υ=3537, 2971, 2935, 2863, 2829, 1752, 1594, 1461, 1332, 1282, 1226, 1091, 1062, 988, 971, 857, 699 cm$^{-1}$.

UV (methanol): λ$_{max}$ (1 g ε)=237 nm (3.84)

MS (70 eV): m/e (%)=656 (1, M+), 638 (1), 502 (4), 484 (2), 313 (4), 295 (13), 189 (32), 157 (96), 91 (99), 71 (100).

Analysis. C$_{36}$H$_{48}$O$_9$S: Calculated: 656.3019. Found: 656.3034 M+.

H-15. Preparation of 5-deoxy-soraphen A (Compound No. 57)

38 mg (58 μmol) of the 5-O-phenylthionocarbonate obtained according to Example H-14 and 4 mg of azoisobutyronitrile (0.1 equivalent) are dissolved in 2 ml of dry toluene, and the solution is treated with 34 mg (2 equivalents) of tributyltin hydride. The solution is flushed with N$_2$ and stirred for 1 hour at 80° C. A TLC (mobile phase: dichloromethane/ether, 4:1, v/v; educt R/ 0.65, product Rf 0.55) shows that the reaction is complete.

The solution is concentrated, the residue is taken up in dichloromethane, the solution is washed with sodium hydrogen carbonate solution and 1N HCl, and the product is purified with the aid of PLC (silica gel Si 60, 0.5 mm, mobile phase: toluene/methanol, 9:1, v/v; R/0.6). Yield: 15 mg=51%

$^1$H-NMR (CDCl$_3$): δ=1.87 (M, 1H, H-6); 1.91 (M, 1H, H-5a); 1.98 (m, 1H, H-5b); 2.42 (m, 1H, H-6); 3.15 (d, 1H, H-4); 3.19 (q, 1H, H-2); 3.83 (s, 3-OH).

$^{13}$C-NMR (CDCl$_3$): δ=26.73 t (c-5); 27.59 d (C-6); 35.78 d (C-8); 98.09 s (C-3); 171.45 s (C-1).

IR (film): $\upsilon = 3540, 3035, 2937, 2892, 2825, 1752, 1662, 1602, 1462, 1362, 1243, 1218, 1150, 1122, 1095, 1058, 1008, 971, 906, 761, 736, 699$ cm$^{-1}$.

UV (methanol): $\lambda_{max}$ (1 g $\epsilon$) = 202 nm (3.97)

MS (70 eV): m/e (%) = 504 (6, M$^+$), 472 (18), 297 (17), 269 (19), 267 (14), 217 (18), 189 (37), 157 (98), 71 (100).

Analysis. $C_{29}H_{44}O_7$: Calculated: 504.3087. Found: 504.3090 M$^+$.

H-16. Preparation of (5R)-soraphen A β-D-glucopyranoside (Compound No. 136)

(a) Oxidation of soraphen A to soraphen A-5-one 500 mg (0.84 mmol) of soraphen A etherate (M = 594.87) are dissolved in 5 ml of dichloromethane, and the solution is treated with 300 mg (1.39 mmol) of pyridinium chlorochromate. The mixture is stirred at room temperature for 24 hours and then filtered over silica gel 60 with CH$_2$Cl$_2$/acetone 95:5. This gives 375 mg (0.72 mmol, 86%) of the product as a pale green oil. For characterization, the crude product can be purified by means of PLC (Merck, silica gel 60, mobile phase: CH$_2$Cl$_2$/acetone 95:5). R$_f$: 0.77 (CH$_2$Cl$_2$/acetone = 90:10). M$^+$: 518

$^1$H-NMR (CDCl$_3$): δ = 3.23 (H-2); 3.18 (H-4); 2.56 (H-6); 4.01 (3-OH).

| $^{13}$C-NMR (CDCl$_3$): | Carbonyl-C | C-4C-7C-17 |
|---|---|---|
| | 207.2 | 74.8/75.7/82.4* |

*unassigned (b) Hydrogenation of 5-keto-soraphen A to (5R)-soraphen A (= 5-epi-soraphen A)

41 mg (0.073 mmol) of soraphen A-5-one are dissolved in 2 ml of absolute methanol, and the solution is treated with 2.8 mg (0.073 mmol) of sodium borohydride. After the reaction mixture has been stirred for 1 hour at room temperature, it is treated with 1N HCl and extracted with ethyl acetate. The combined organic phases are washed with 5% sodium hydrogen carbonate solution and concentrated NaCl solution, dried over sodium sulfate and concentrated in vacuo. This gives 42 mg of the crude product which is purified by means of PLC (silica gel 60, mobile phase: CH$_2$Cl$_2$/acetone 90:10).

This gives 32 mg (0.06 mmol, 82%) of (5R)-soraphen A as a white solid.

R$_f$: 0.44 (CH$_2$Cl$_2$/acetone = 90:10)
M$^+$ = 520

$^1$H-NMR (CDCl$_3$): δ = 3.14 (H-2); 3.35 (H-4); 4.12 (H-5); 2.02 (H-6); 2.50 (H-8); 3.76 (3-OH); 1.89 (5-OH).

| $^{13}$C-NMR (CDCl$_3$): | Carbonyl-C | C-4/C-5/C-7/C-17 |
|---|---|---|
| | 170.9 | 70.3/74.7/76.8/79.9* |

*unassigned

This compound, which is epimeric to soraphen A, is part of the subject-matter of the invention of EP-A-282,455 and of parallel patent applications.

(c) Preparation of (5R)-soraphen A 2',3',4',6'-tetra-O-acetyl-β-D-glucopyranoside 23 mg (44 μmol) of (5R)-soraphen A, obtained in procedure (b), 100 mg of anhydrous CaSO$_4$ in the form of granules and 50 mg of silver silicate (freshly prepared in a 1:1 precipitation of Na water-glass and AgNO$_3$ and precipitated on Al$_2$O$_3$) are stirred for 30 minutes in 1 ml of dry dichloromethane. To this is added a solution of 45 mg of α-acetobromoglucose (2.5 equivalents) in 0.3 ml of dichloromethane, and the mixture is stirred for 48 hours at RT. A TLC (mobile phase: dichloromethane/acetone, 9:1, v/v; educt R$_f$ 0.3, product R$_f$ 0.45) shows partial reaction.

The solution is filtered and concentrated, and the product is purified with the aid of PLC (silica gel Si 60, 1 mm, mobile phase: dichloromethane/acetone, 9:1, v/v; R$_f$ 0.4). Yield: 4.5 mg = 12%

$^1$H-NMR (CDCl$_3$): δ = 2.09 (m, 1H, H-6); 2.53 (m, 1H, H-8); 3.18 (q, 1H, H-2); 3.33 (d, 1H, H-4); 4.18 (m, 1H, H-5); 3.92 (s, 3-OH); 2.00, 2.01, 2.05, 2.10 (s, 3 H, tetraacetyl); 3.71, 4.16, 4.33, 4.60, 5.07, 5.12, 5.23 (glucose).

MS (70 eV): m/e (%) = 850 (2, M$^+$), 832 (1), 818 (2), 470 (2), 331 (31), 217 (5), 189 (11), 169 (77), 157 (50), 43 (100).

(d) Hydrolysis to (5R)-soraphen A-β-D-glucopyranoside 8.5 mg (10 μmol) of (5R)-soraphenyl-2',3',4',6'-tetra-O-acetyl-β-D-glucopyranoside are dissolved in 0.5 ml of methanol, and the solution is treated with 0.1 ml of concentrated ammonia solution. After 2 hours, a TLC (mobile phase: dichloromethane/methanol, 9:1, v/v; educt R$_f$ 0.8, educt R$_f$ 0.8, product R$_f$ 0.2) shows that the reaction is complete.

The product is purified directly from the reaction solution with the aid of PLC (silica gel Si 60, 0.5 mm, mobile phase: dichloromethane/methanol, 9:1, v/v; R$_f$ 0.2). Yield: 2.2 mg = 33%

$^1$H-NMR (CDCl$_3$): δ = 2.52 (m, 1H, H-8); 3.19 (q, 1H, H-2); 4.23 (m, 1H, H-5); 4.45 (d, 1H, H-1", glucose)

MS (FAB): m/e (%) = 681 [30, (m-H)$^-$], 519 (7), 505 (20), 501 (15).

The corresponding β-D-glucopyranoside and other saccharides of the natural seraphen A are obtained analogously.

H-17. Preparation of 5-tert-butyldimethylsilyloxy-9,10-dihydro-soraphen A (Compound No. 119)

100 mg of compound No. 73 (see Example H-6) are dissolved in 5 ml of methylene chloride and hydrogenated for 1 hour at 25° C. and at an H$_2$ pressure of 1 atm, with the addition of 50 mg [iridium (cyclooctadiene) (acetonitrile) (tricyclohexylphosphine)tetrafluoroborate. The mixture is distributed between ethyl acetate and water, dried and concentrated. Chromatography on silica gel with ethyl acetate/hexane (1:4) as the mobile phase gives 76 mg (76% of theory) of compound No. 119.

MS: m/e = 636

$^1$H-NMR (250 MHz; d$_6$-acetone): 5.86 (H-17); 5.22 (OH); 4.37 (OH); 3.98 (H-7).

R$_f$(ethyl acetate/hexane 1:3) = 0.19

H-18. Preparation of 9,10-dihydro-soraphen A 5-formate (Compound No. 18)

(a) Preparation of 9,10-dihydro-soraphen A 35 mg of compound No. 119 are stirred for 10 minutes at room temperature in 2 ml of 1N tetrabutylammonium fluoride solution. The mixture is distributed between ethyl acetate and water, dried and concentrated. Chromatography on silica gel with ethyl acetate/hexane (1:3) as the mobile phase yields 22 mg of product.

$R_f$(ethyl acetate/hexane=1:1)=0.36
MS: m/e=522
$^1$H-NMR (250 MH$_2$; d$_6$-acetone): 5.84 (H-17); 5.36 (OH); 4.24 (OH); 3.98 (H-7).

(b) Preparation of 9,10-dihydro-soraphen A 5-formate 25 mg of compound No. 127 and 5.9 mg of 4-dimethylaminopyridine are dissolved in 2 ml of dry dichloromethane, and the solution is treated with 5.9 mg of HCOOH and 24.5 mg of triethylamine. The mixture is cooled to 10° C., treated with 10 mg of acetic anhydride and stirred for 30 minutes.

The ice-bath is removed, and stirring is continued for 30 minutes at room temperature. The reaction mixture is then treated with a few drops of methanol and concentrated. The residue is treated with water and extracted several times with ethyl acetate. The combined organic phases are washed in succession with 1N HCl (pH 0), 5% sodium hydrogen carbonate solution (pH 8) and with a concentrated solution of sodium chloride (pH 6). The mixture is then dried over sodium sulfate and concentrated on a rotary evaporator.

This gives 24.8 mg of 9,10-dihydro-soraphen A 5-formate, $R_f$(dichloromethane/acetone=9:1) 0.68, which is NMR-spectroscopically uniform.

In this way or following one of the methods indicated further above, the following soraphen derivatives of the formula I can be obtained. In the Table below, "DB" indicates a double bond in the 9,10-position.

TABLE 3

| No. | R | 9,10-Position | $R_o$ |
|---|---|---|---|
| 1 | CH$_3$ | DB | O—CHO |
| 2 | H | — | O—CHO |
| 3 | CHO | — | O—CHO |
| 4 | CH$_3$ | DB | O—CO—CH$_3$ |
| 5 | CH$_3$ | DB | O—CO—CF$_3$ |
| 6 | CH$_3$ | DB | O—CO—C$_2$H$_5$ |
| 7 | CH$_3$ | DB | O—CO—C$_3$H$_7$ |
| 8 | CH$_3$ | DB | O—CO-iso-C$_3$H$_7$ |
| 9 | CH$_3$ | DB | O—CO—C$_6$H$_{13}$ |
| 10 | COCH$_3$ | — | O—CO—CH$_3$ |
| 11 | COC$_3$H$_7$ | — | O—CO—C$_3$H$_7$ |
| 12 | H | — | O—CO—CH$_3$ |
| 13 | H | — | O—CO—C$_3$H$_7$ |
| 14 | H | — | O—CO-phenyl |
| 15 | CH$_3$ | DB | O—CO-phenyl |
| 16 | COCF$_3$ | — | O—CO—CF$_3$ |
| 17 | CO-cyclohexyl | — | O—CO-cyclohexyl |
| 18 | CH$_3$ | — | O—CHO |
| 19 | CH$_3$ | DB | O—CO-benzyl |
| 20 | CH$_3$ | DB | O—CO—CH$_2$—(4-NO$_2$-phenyl) |
| 21 | H | — | O—CO—CH$_2$—(4-OCH$_3$-phenyl) |
| 22 | CH$_3$ | DB | O—CO—(4-CF$_3$-phenyl) |
| 23 | CH$_3$ | DB | O—CO—(4-Cl-phenyl) |
| 24 | CH$_3$ | DB | O—CO—(3,4-di-CH$_3$-phenyl) |
| 25 | CH$_3$ | DB | O—CO—CCl$_3$ |
| 26 | CH$_3$ | DB | O—CO—CH$_2$SCH$_3$ |
| 27 | CH$_3$ | DB | O—CO—CH$_2$O-phenyl |
| 28 | CH$_3$ | DB | O—CO—CH$_2$O-cyclopropyl |

TABLE 3-continued

| No. | R | 9,10-Position | $R_o$ |
|---|---|---|---|
| 29 | $CH_3$ | — | $O-CO-(CH_2)_6OC_3H_7$ |
| 30 | H | — | $O-CO-CH_2-C\equiv C-H$ |
| 31 | $CH_3$ | DB | $O-CO-(CH_2)_4-C\equiv C-H$ |
| 32 | $CH_3$ | DB | $O-CO-CH=CH_2$ |
| 33 | $COCH_3$ | — | $O-CO-(CH_2)_4-CH=CH_2$ |
| 34 | $COCF_3$ | — | $O-CO-CH=CH-CH_3$ (trans) |
| 35 | $CH_3$ | DB | $O-CS-CH_3$ |
| 36 | $CH_3$ | DB | $O-CHS$ |
| 37 | $CH_3$ | DB | $O-CS$-benzyl |
| 38 | $COCH_3$ | — | $O-CS-CH_2OCH_3$ |
| 39 | $CH_3$ | DB | $O-CS$-cyclopropyl |
| 40 | H | — | $O-CS$-cyclohexyl |
| 41 | $CH_3$ | DB | $O-CS-CH=CH_2$ |
| 42 | $CH_3$ | DB | $O-CS-C\equiv C-H$ |
| 43 | $COCH_3$ | — | $O-CO-CHCl_2$ |
| 44 | $CH_3$ | DB | $O-CO-CHF_2$ |
| 45 | H | — | $O-CO-CF_2Cl$ |
| 46 | $CH_3$ | DB | $O-CO-C_3F_7$ |
| 47 | $CH_3$ | DB | $O-CO-CH_2OCH_3$ |
| 48 | $CH_3$ | DB | $O-CO-C\equiv C-H$ |
| 49 | $CH_3$ | DB | $O-CO-CH(CH_3)=CH(CH_3)$[tiglate] |
| 50 | $COCH_2OCH_3$ | — | $O-CO-CH_2OCH_3$ |
| 51 | $CH_3$ | DB | $O-CO$-cyclopropyl |
| 52 | $COCHCl_2$ | — | $O-CO-CHCl_2$ |
| 53 | $CH_3$ | DB | $O-CO-CH_2NH_2$ |
| 54 | $CH_3$ | DB | $O-CO-CH(CH_3)OH$ |
| 55 | $CH_3$ | DB | $O-CO-CH_2CH_2COOH$ |
| 56 | H | — | H |
| 57 | $CH_3$ | DB | H |
| 58 | $CH_3$ | — | H |
| 59 | $COCH_3$ | — | H |
| 60 | $CH_3$ | DB | F |
| 61 | $CH_3$ | DB | Cl |
| 62 | $CH_3$ | DB | Br |
| 63 | $CH_3$ | DB | I |
| 64 | $COCH_3$ | — | Cl |
| 65 | $CO$-cyclopropyl | — | F |
| 66 | $CO(CH_2)_6I$ | — | H |
| 67 | $CH_3$ | DB | $O-Si(CH_3)_3$ |
| 68 | $CH_3$ | DB | $O-Si(CH_3)_2$(phenyl) |
| 69 | H | — | $O-Si(CH_3)_2$(thexyl) |
| 70 | CHO | — | $O-Si$(phenyl)$_3$ |
| 71 | $CO$cyclopropyl | — | $O-Si(CH_3)_2$-cyclohexyl |
| 72 | $CH_3$ | DB | $O-Si(CH_3)_2$-cyclohexyl |
| 73 | $CH_3$ | DB | $O-Si(CH_3)_2$-tert.butyl |
| 74 | $CH_3$ | DB | $O-SO_2CH_3$ |
| 75 | $CH_3$ | DB | $O-SO_2-\langle C_6H_4 \rangle-CH_3$ |
| 76 | H | — | $O-SO_2-C_4H_9$ |
| 77 | $CH_3$ | DB | $O-SO_2-\langle C_6H_4 \rangle-CF_3$ |
| 78 | $COCH_3$ | — | $O-SO_2-\langle C_6H_4 \rangle-OCH_3$ |
| 79 | $CH_3$ | DB | $O-SO_2-\langle C_6H_4 \rangle-Cl$ |
| 80 | $COCF_3$ | — | $O-SO_2$-cyclohexyl |
| 81 | $CH_3$ | DB | $O-SO_3Na$ |
| 82 | $CH_3$ | DB | $O-CH_2-C\equiv C-H$ |
| 83 | $CH_3$ | — | $O-(CH_2)_4-C\equiv C-H$ |

TABLE 3-continued

| No. | R | 9,10-Position | $R_o$ |
|---|---|---|---|
| 84 | $CH_3$ | DB | $O-CH_2-CH=CH_2$ |
| 85 | $COCH_3$ | — | $O-(CH_2)_4-CH=CH_2$ |
| 86 | $COCH_2OCH_3$ | — | $O-CH_2-CH=CH_2$ |
| 87 | CHO | — | $O-CH_2-CH=CH-CH_3$ (trans) |
| 88 | $CH_3$ | DB | $O-CH_2-COOH$ |
| 89 | $CH_3$ | DB | $O-CH_2CH_2-NH_2$ |
| 90 | $CH_3$ | DB | $O-CH_2-CH(OH)(phenyl)$ |
| 91 | $CH_3$ | DB | $O-CH_2-CO-phenyl$ |
| 92 | $CH_3$ | DB | $O-CH_3$ |
| 93 | $CH_3$ | DB | $O-CH_2OCH_3$ |
| 94 | $CH_3$ | DB | $O-(CH_2)_6OC_3H_7n$ |
| 95 | $CH_3$ | DB | O-cyclopropyl |
| 96 | $CH_3$ | DB | O-cyclohexyl |
| 97 | $COCH_3$ | — | $O-CH_2-S-CH_3$ |
| 98 | H | — | $O-C_6H_{13}n$ |
| 99 | $CH_3$ | DB | O-phenyl |
| 100 | $CH_3$ | DB | O-benzyl |
| 101 | $CH_3$ | DB | $O-CH_2-$(2-nitrophenyl) |
| 102 | H | — | $O-CH_2-$(4-methoxyphenyl) |
| 103 | $COCH_3$ | — | $O-$(4-trifluoromethylphenyl) |
| 104 | $CH_3$ | DB | $O-$(4-hydroxyphenyl) |
| 105 | $COCF_3$ | — | $-O-CH_2-$(2,6-dimethylphenyl) |
| 106 | $CH_3$ | DB | $O-CH_2-$(4-chlorophenyl) |
| 107 | $CH_3$ | DB | $OCH_2CH_2Br$ |
| 108 | $CH_3$ | DB | $OCH_2CF_3$ |
| 109 | $CH_3$ | DB | $OCH_2-S-CH_3$ |
| 110 | $CH_3$ | — | $OCOCH_3$ |
| 111 | $CH_3$ | — | $OCOCF_3$ |
| 112 | $CH_3$ | — | $OCOCCl_3$ |
| 113 | $CH_3$ | — | $OCOCH_2OCH_3$ |
| 114 | $CH_3$ | — | $OCOC_6H_5$ |
| 115 | $CH_3$ | — | $OCS-C_6H_5$ |
| 116 | $CH_3$ | — | Br |
| 117 | $CH_3$ | DB | $N_3$ |
| 118 | H | — | $N_3$ |
| 119 | $CH_3$ | — | $OSi(CH_3)_2$ tert.butyl |
| 120 | $CH_3$ | — | $OSO_2CH_3$ |
| 121 | $CH_3$ | — | $OCH_3$ |

TABLE 3-continued

| No. | R | 9,10-Position | $R_o$ |
|---|---|---|---|
| 122 | $CH_3$ | — | 2-nitro-phenyl-OCH$_2$– (OCH$_2$-C$_6$H$_4$-NO$_2$) |
| 123 | $CH_3$ | — | $OCONH_2$ |
| 124 | $CH_3$ | — | β-glucopyranosyloxy (β-form) |
| 125 | $CH_3$ | DB | β-furanosyl sugar (β-form) |
| 126 | $CH_3$ | — | $OCS-OCH_3$ |
| 127 | CHO | — | OH |
| 128 | $CH_3$ | DB | $O-C_6H_{13}$ |
| 129 | $CH_3$ | DB | $O-CH_2$-C$_6$H$_4$-$OCH_3$ |
| 130 | $CH_3$ | DB | $O-CH_2$-C$_6$H$_4$-$CF_3$ |
| 131 | $CH_3$ | DB | 1,3-dioxan-2-yloxy |
| 132 | $CH_3$ | DB | 1,3-oxathian-2-yloxy |
| 133 | H | — | 1,3-dioxolan-2-yloxy |
| 134 | $CH_3$ | DB | 1,3-oxathiolan-2-yloxy |
| 135 | $CH_3$ | DB | $O-CH_2OCH_2CH_2OCH_3$ |

TABLE 3-continued

| No. | R | 9,10-Position | $R_o$ |
|---|---|---|---|
| 136 | $CH_3$ | DB | 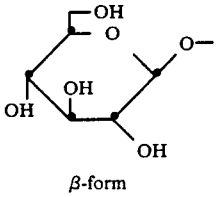 β-form (sugar with OH groups, O—) |
| 137 | $CH_3$ | DB | 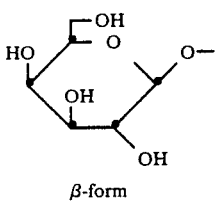 β-form |
| 138 | $CH_3$ | DB | 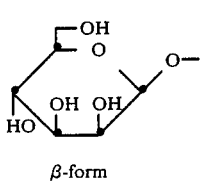 β-form |
| 139 | $CH_3$ | DB | O—CO—$NH_2$ |
| 140 | H | — | O—CO—$NHCH_3$ |
| 141 | $CH_3$ | DB | O—CO—NH(phenyl) |
| 142 | $CH_3$ | DB | O—CO—N(iso-propyl)(cyclohexyl) |
| 143 | $CH_3$ | DB | O—CO—N($C_6H_{13}n)_2$ |
| 144 | $COCH_3$ | — | O—CO—NH(cyclopropyl) |
| 145 | $CH_3$ | DB | O—CS—$NH_2$ |
| 146 | $CH_3$ | DB | O—CS—NH(phenyl) |
| 147 | $CH_3$ | DB | O—CO—NH(cyclopropyl) |
| 148 | $CH_3$ | DB | O—CO—$NHCH_3$ |
| 149 | $CH_3$ | DB | O—CO—$OCH_3$ |
| 150 | H | — | O—CO—$OC_6H_{13}$ |
| 151 | $CH_3$ | DB | O—CO—O-cyclohexyl |
| 152 | $COCH_3$ | — | O—CO—O-cyclopropyl |
| 153 | $CH_3$ | DB | O—CO—O-phenyl |
| 154 | $CH_3$ | DB | O—CS—$OCH_3$ |
| 155 | H | — | O—CS—O-phenyl |
| 156 | $CH_3$ | DB | O—CS—O-cyclohexyl |
| 157 | $CH_3$ | DB | O—CO—$SCH_3$ |
| 158 | $CH_3$ | DB | O—CS—$SC_6H_{13}n$ |
| 159 | H | — | O—CO—S-phenyl |
| 160 | $COCH_3$ | — | O—CS—S-Cyclohexyl |
| 161 | $CH_3$ | DB | O—CO—S-Cyclopropyl |
| 162 | $CH_3$ | DB | O—CS—S-iso-propyl |
| 163 | $CH_3$ | DB | O—CO—S-phenyl |
| 164 | $CH_3$ | DB | O—CS—$SCH_3$ |
| 165 | $COCH_3$ | — | OH |
| 166 | $COC_4H_9$ | — | OH |
| 167 | $COCH_3$ | — | OH |
| 168 | $COCH_2OCH_3$ | — | OH |
| 169 | CO-cyclopropyl | — | OH |
| 170 | $CH_3$ | DB | O—CO—O-tert. $C_4H_9$ |
| 171 | $CH_3$ | DB | O—CO—$C(CH_3)_3$ |
| 172 | $CH_3$ | DB | O-2,4-dinitrophenyl |
| 173 | $CH_3$ | DB | O—CS—O-phenyl |
| 174 | $CH_3$ | DB | O—Si$(OH)$(tert.butyl)$_2$ |
| 175 | $CH_3$ | — | O—CO—$CCl_3$ |
| 176 | H | — | O—CO—$CCl_3$ |
| 177 | $CH_3$ | — | O—CO—$CH_2NH_2$ |
| 178 | H | — | O—CO—$CH_2NH_2$ |

2. Formulation examples of the active substance of the formula I (%=percent by weight)

["Active substance" in the following denotes an active substance from the previous Table]

| 2.1 Emulsion concentrates | a | b | c |
|---|---|---|---|
| Active substance | 25% | 40% | 50% |
| Ca dodecylbenzenesulfonate | 5% | 8% | 6% |
| Castor oil polyethylene glycol ether (36 mol of ethylene oxide) | 5% | — | — |
| Tributylphenol polyethylene glycol ether (30 mol of ethylene oxide) | — | 12% | 4% |

-continued

| 2.1 Emulsion concentrates | a | b | c |
|---|---|---|---|
| Cyclohexanone | — | 15% | 20% |
| Xylene mixture | 65% | 25% | 20% |

Emulsions of any desired concentration can be prepared from such concentrates by dilution with water.

| 2.2 Solutions | a | b | c | d |
|---|---|---|---|---|
| Active substance | 80% | 10% | 5% | 95% |
| Ethylene glycol monomethyl ether | 20% | — | — | — |
| Polyethylene glycol MW 400 | — | 70% | — | — |
| N-Methyl-2-pyrrolidone | — | 20% | — | — |
| Epoxidized coconut oil | — | — | 1% | 5% |
| Naphtha (boiling range 160–190° C.) | — | — | 94% | — |

(MW = molecular weight)

The solutions are suitable for application in the form of micro droplets.

| 2.3 Granules | a | b |
|---|---|---|
| Active substance | 5% | 10% |
| Kaolin | 94% | — |
| Highly-disperse silicic acid | 1% | — |
| Attapulgite | — | 90% |

The active substance is dissolved in methylene chloride, the solution is sprayed onto the carrier, and the solvent is then evaporated in vacuo.

| 2.4 Dusting agents | a | b |
|---|---|---|
| Active substance | 2% | 5% |
| Highly-disperse silicic acid | 1% | 5% |
| Talc | 97% | — |
| Kaolin | — | 90% |

Intimate mixing of the carrier substances with the active substance gives ready-to-use dusts. With the further addition of the three carrier substances, these dusting agents can be ground to give dusts ready for application containing 0.001% of active substance.

| 2.5 Wettable powders | a | b | c |
|---|---|---|---|
| Active substance | 25% | 50% | 75% |
| Na ligninsulfonate | 5% | 5% | —% |
| Na laurylsulfate | 3% | — | 5% |
| Na diisobutylnaphthalenesulfonate | — | 6% | 10% |
| Octylphenol polyethylene glycol ether (7–8 mol of ethylene oxide) | — | 2% | —% |
| Highly-disperse silicic acid | 5% | 10% | 10% |
| Kaolin | 62% | 27% | — |

The active substance is thoroughly mixed with the additives, and the mixture is thoroughly ground in a suitable mill. This gives wettable powders which can be diluted with water to give suspensions of any desired concentration.

| 2.6 Coated granules | |
|---|---|
| Active substance | 3% |
| Polyethylene glycol (MW 200) | 3% |
| Kaolin | 94% |

(MW = molecular weight)

In a mixer, the kaolin moistened with polyethylene glycol is evenly coated with the finely-ground active substance. In this manner, dust-free coated granules are obtained.

| 2.7 Suspension concentrate | |
|---|---|
| Active substance | 40% |
| Ethylene glycol | 10% |
| Nonylphenol polyethylene glycol ether (15 moles of ethylene oxide) | 6% |
| Na ligninsulfonate | 10% |
| Carboxymethylcellulose | 2% |
| 37% aqueous formaldehyde solution | 0.2% |
| Silicone oil in the form of a 75% aqueous emulsion | 0.8% |
| Water | 32% |

The finely ground active substance is intimately mixed with the additives. This gives a suspension concentrate, from which suspensions of any desired concentration can be prepared by dilution with water.

3. Biological examples on plants (In the following "active substance" denotes a preparation from Table 3, unless stated otherwise).

Example 3.1: Action against *Puccinia graminis* on wheat (a) Residual-protective action 6 days after sowing, wheat plants are sprayed with a spray liquor (0.02% of active ingredient) prepared from a wettable powder of the active substance. After 24 hours, the treated plants are infected with a uredospore suspension of the fungus. After incubation for 48 hours at 95–100% relative atmospheric humidity and about 20° C., the infected plants are placed in a greenhouse at about 22° C. The development of rust pustules is assessed 12 days after infection.

(b) Systemic action 5 days after sowing, a spray liquor (0.002% active ingredient relative to the soil volume) which is prepared from a wettable powder of the active substance, is poured onto wheat plants. After 48 hours, the treated plants are infected with a uredospore suspension of the fungus.

After incubation for 48 hours at 95–100% relative atmospheric humidity and about 20° C., the infected plants are placed in a greenhouse at about 22° C. The development of rust pustules is assessed 12 days after the infection.

In both experiments, fungal infestation was inhibited completely by active substances of the formula I. In experiment (a), compounds Nos. 2, 18, 25, 47, 55, 175, 176, 113, 136, 177, 178 and others showed complete inhibition (0–5% fungal infestation), even at a dilution of 0.006%.

In contrast, untreated, infected control plants showed 100% infestation with Puccinia.

Example 3.2: Action against Phytophthora on tomato plants (a) Residual-protective action After 3 weeks' growing period, tomato plants were sprayed with a spray liquor (0.02% of active ingredient) which had been prepared from a wettable powder of the active substance. After 24 hours, the treated plants were infected with a Sporangia suspension of the fungus. Fungal infestation was assessed after the infected plants had been incubated for 5 days at 90-100% relative atmospheric humidity and 20° C.

(b) Systemic action

After 3 weeks' growing period, a spray liquor (0.002% of active ingredient relative to the soil volume) which had been prepared from a wettable powder of the active substance, was poured onto tomato plants. Care was taken that the spray liquor did not come into contact with the aerial parts of the plants. After 48 hours, the treated plants were infected with a sporangia suspension of the fungus. Fungal infestation was assessed after the infected plants had been incubated for 5 days at 90-100% relative atmospheric humidity and 20° C.

In both experiments, no fungal infestation was observed during the evaluation. In experiment (a), compounds Nos. 1, 2, 18, 25, 47, 55, 113, 136, 175, 176 and others caused complete inhibition of infestation with disease (=0-5% infestation), even at a dilution of 0.006%.

Example 3.3: Action against *Plasmopara viticola* on vines

Residual-protective action

Vine seedlings in the 4-5 leaf stage were sprayed with a spray liquor (0.006% of active ingredient) which had been prepared from a wettable powder of the active substance. After 24 hours, the treated plants are infected with a sporangia suspension of the fungus. After the plants have been incubated for 6 days at 95-100% relative atmospheric humidity and 20° C., the fungal infestation is assessed.

In contrast to the untreated, infected control plants where fungal infestation was 100%, the plants which had been treated with active substance I were free from infestation, for example those treated with compound Nos. 1, 2, 4, 10, 18, 25, 47, 113, 136, 175 or 176.

Example 3.4: Action against *Cercospora arachidicola* on peanut plants

Residual-protective action

Peanut plants 10-15 cm in height are sprayed with a spray liquor (0.006% of active ingredient) which has been prepared from a wettable powder of the active substance, and, 48 hours later, infected with Conidia suspension of the fungus. The infected plants are incubated for 72 hours at about 21° C. and a high atmospheric humidity and then placed in a greenhouse until the typical leaf spots occur. The fungicidal action is assessed 12 days after the infection with regard to number and size of the spots which occur.

The plants which had been treated with active substance I, for example with compound Nos. 1, 2, 4, 8, 10, 18, 25, 47, 55, 73, 113, 131, 136, 53, 172, 175, 176, 177 and 178 were free from infestation. In contrast, untreated, infected control plants showed infestation with Cercospora of 100%.

Example 3.5: Action against *Venturia inaequalis* on apple shoots

Residual-protective action

Apple seedlings having fresh shoots of 10-20 cm length are sprayed with a spray liquor (0.02% of active ingredient) which has been prepared from a wettable powder of the active substance. After 24 hours, the treated plants are infected with a conidia suspension of the fungus. The plants are then incubated for 5 days at 90-100% relative atmospheric humidity and placed for 10 more days in a greenhouse at 20°-24° C. Scab infestation is assessed 15 days after the infection.

The cuttings treated with active substance I were free from infestation. With compounds Nos. 1, 2, 6, 7, 10, 18, 25, 47, 49, 55, 84, 113, 136, 53 and 177, infestation with disease was completely prevented (0-5% infestation) even at a dilution of 0.006%.

Example 3.6: Action against *Botrytis cinerea* on apple fruits

Residual-protective action

Artificially damaged apples are treated by applying dropwise a spray liquor (0.02% of active ingredient) which has been prepared from a wettable powder of the active substance, to the damaged points. The treated fruits are then inoculated with a spore suspension of the fungus and incubated for one week at high atmospheric humidity and about 20° C. In the evaluation, the damaged points which show signs of rotting are counted, and the fungicidal action of test substance is calculated therefrom.

Active substance I completely inhibited the growth of the fungi. With compounds Nos. 1, 2, 4, 6, 7, 8, 15, 18, 25, 32, 47, 49, 55, 57, 73, 74, 53, 75, 84, 92, 113, 124, 131, 136, 139, 141, 149, 165, 168 and 170-178, infestation with disease was prevented completely (0-5% infestation) even at a dilution of 0.006%.

Example 3.7: Action against *Erysiphae graminis* on barley (a) Residual-protective action Barley plants approximately 8 cm in height are sprayed with a spray liquor (0.006% of active ingredient) which has been prepared from a wettable powder of the active substance). After 3-4 hours, the treated plants are dusted with conidia of the fungus. The infected barley plants are placed in a greenhouse at about 22° C., and fungal infestation is assessed after 10 days.

(b) Systemic action

A spray liquor (0.002% of active ingredient relative to the soil volume) which has been prepared from a wettable powder of the active substance, is poured onto barley plants approximately 8 cm in height. Care was taken that the spray liquor did not come into contact with the aerial parts of the plants. After 48 hours, the treated plants are dusted with conidia of the fungus. The infected barley plants are placed in a greenhouse at about 22° C., and fungal infestation is assessed after 10 days.

In both experiments, the plants were free from infestation, and the control plants were completely diseased. In Experiment (a), compounds Nos. 1, 3-8, 12-15, 18, 22, 25, 32, 47, 49, 50, 53, 55, 57, 67, 73, 74, 75, 84, 92, 100, 113, 124, 127, 131, 136, 139, 141, 149, 165, 168 and 170-178 caused complete inhibition of infestation with the disease (0-5%), even at a dilution of 0.002%.

Example 3.8: Action against *Rhizoctonia solani* (soil-borne fungus on rice plants)

Protective-local soil application

A spray liquor (0.002% of active ingredient) which has been prepared from a preparation of the active substance, is poured onto 12-day old rice plants without

37 contaminating the aerial parts of the plants. To infect the treated plants, a suspension of *mycelium* and *sclerotia* of *R. solani* is placed on the soil surface. After incubation for 6 days at 27° C. (day) and 23° C. (night) and 100% relative atmospheric humidity (humid chamber) in a growth cabinet, the fungal infestation on leaf sheath, leaves and stem is assessed.

No infestation occurred after treatment with active substance I.

Example 3.9: Action against *Pyricularia oryzae* on rice plants (a) Residual-protective action After a growing period of two weeks, rice plants are sprayed with a spray liquor (0.006% of active ingredient) which has been prepared from a wettable powder of the active substance. After 48 hours, the treated plants are infected with a conidia suspension of the fungus. After incubation for 5 days at 95-100% relative atmospheric humidity and 24° C., fungal infestation is assessed.

(b) Systemic action

A spray liquor (0.002% of active ingredient relative to the soil volume) which has been prepared from a wettable powder of the active substance is poured onto two-week-old rice plants growing in flower pots. The pots are then filled with water in such a way that the lower parts of the stems of the rice plants are submerged. After 48 hours, the treated plants are infected with a conidia suspension of the fungus. After the infected plants have been incubated for 5 days at 95-100% relative atmospheric humidity and about 24°, the fungal infestation is assessed.

Compounds from the tables showed a long-term action against the fungus Pyricularia (infestation less than 20%). In contrast, untreated, infected control plants showed an infestation of 100%.

Complete inhibition of infestation with disease was achieved with compounds Nos. 1, 2, 4, 6, 7, 8, 18, 25, 47, 55, 124 and others (0–5% infestation).

We claim:
1. A macrocyclic compound of the formula I

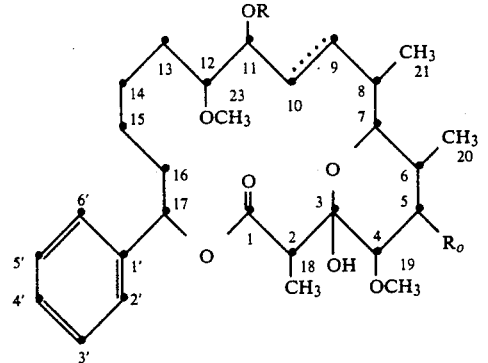

in which the dotted line in the 9,10-position is a saturated bond or a double bond alternatively, while R is hydrogen, $CH_3$ or —COA, where A is hydrogen or $C_3$-$C_6$cycloalkyl, or is $C_1$-$C_6$alkyl which is unsubstituted or substituted by halogen or $C_1$-$C_3$alkoxy, and $R_o$ is hydrogen, halogen, —$N_3$, —SH, —OH or —OY, and Y, alternatively, (a) is a $C_3$-$C_6$alkenyl or $C_3$-$C_6$alkynyl group, a $C_1$-$C_6$alkyl group which is unsubstituted or substituted by halogen, hydroxy, $C_1$-$C_6$alkoxy, $C_1$-$C_6$alkylthio, carboxy, amino, $C_3$-$C_6$cycloalkyl or one or two phenyl or phenoxy groups said phenyl or phenoxy groups being unsubstituted or substituted in the aromatic ring by $C_1$-$C_4$alkyl, halogen, hydroxy, $C_1$-$C_4$alkoxy, —$CF_3$ or —$NO_2$, an alkoxyalkoxyalkyl group having up to 10 C atoms, a $C_3$-$C_6$cycloalkyl group or phenyl group which is unsubstituted or substituted by $C_1$-$C_4$alkyl, halogen, hydroxy, $C_1$-$C_4$alkoxy, —$CF_3$ or —$NO_2$, or (b) is a silyl group —$SiR_1R_2R_3$, in which $R_1$-$R_3$ independently are $C_1$-$C_6$alkyl, phenyl, benzyl or $C_3$-$C_6$cycloalkyl, or (c) is —$SO_2Z$, where Z is the group —OM, in which M is hydrogen or the mole equivalent of a metal, or where Z is $C_1$-$C_6$alkyl, phenyl, naphthyl or diphenyl; or (d) is a group

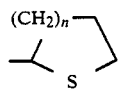

where n is 1 or 2 or is a group

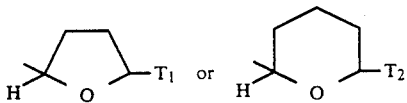

which is unsubstituted or, like a furanose or pyranose, completely or partly substituted by —OH and in which $T_1$ is hydrogen, —OH, —$CH_2OH$ or —CHOH—$CH_2OH$ and $T_2$ is hydrogen, —OH or —$CH_2OH$, or (e) is —CO—B or —CS—B, where B is hydrogen or $C_1$-$C_6$alkyl which is unsubstituted or substituted by halogen, hydroxy, $C_1$-$C_6$alkoxy, $C_1$-$C_6$alkylthio, carboxy, amino, $C_3$-$C_6$cycloalkyl or one or two phenyl or phenoxy groups said phenyl or phenoxy groups being unsubstituted or substituted in the aromatic ring by $C_1$-$C_4$alkyl, halogen, hydroxy, $C_1$-$C_4$alkoxy, —$CF_3$ or —$NO_2$, or is $C_2$-$C_6$alkenyl, $C_2$-$C_6$alkynyl, $C_3$-$C_6$cycloalkyl or phenyl which is unsubstituted or substituted by $C_1$-$C_4$alkyl, halogen, hydroxy, $C_1$-$C_4$alkoxy, —$CF_3$ or —$NO_2$, or one of the groups —$N(R_4)(R_5)$, —$OR_6$ or —$SR_6$, $R_4$ and $R_5$ independently of one another are hydrogen, $C_1$-$C_6$alkyl, $C_1$-$C_6$haloalkyl, $C_3$-$C_6$alkenyl, $C_3$-$C_6$alkynyl, $C_3$-$C_6$cycloalkyl or phenyl, and $R_6$ is $C_1$-$C_6$alkyl, $C_3$-$C_6$cycloalkyl or phenyl, with the proviso that R is methyl if a double bond is present in the 9,10-position, and that R is the group —COA if $R_o$ is an OH group, said macrocyclic compound being in the 3-hemiacetal form of formula (I) or the 3-keto-7-hydroxy from or a mixture of both forms.

2. A compound according to claim 1, in which R is methyl and $R_o$ is halogen, azido, thiol, hydroxyl or OY, where Y has the meanings mentioned under (a), (b), (c), (d) and (e).

3. A compound according to claim 2, where Y has the meaning mentioned under (a).

4. A compound according to claim 2, where Y has the meaning mentioned under (d).

5. A compound according to claim 4, where Y is a tetrahydrofuranyl or tetrahydropyranyl ring which is substituted by hydroxyl and —CH$_2$OH.

6. Soraphenyl-$\beta$-D-glucopyranoside and (5R)-soraphenyl-$\beta$-D-glucopyranoside according to claim 5.

7. A compound according to claim 2, where Y has the meaning of the acylation mentioned under (e).

8. A compound according to claim 7, selected from amongst soraphen A 5-methoxyacetate, soraphen A 5-trichloroacetate, soraphen A 5-formate, soraphen A 5-aminoacetate, 9,10-dihydro-soraphen A 5-formate, 9,10-dihydro-soraphen A 5-methoxyacetate and 9,10-dihydro-soraphen A 5-aminoacetate.

9. A compound according to claim 1, in which R is hydrogen or the group —COA, where A is hydrogen, C$_3$–C$_6$cycloalkyl or C$_1$–C$_6$alkyl which is unsubstituted or substituted by halogen or C$_1$–C$_3$alkoxy while R$_o$ is hydrogen, azido, halogen, hydroxyl or thiol.

10. A compound of claim 1 which is in the 3-hemiacetal form of formula I.

11. A compound of claim 1 which is in the open 3-keto-7-hydroxy form.

12. A compound of claim 1 which is a mixture of the 3-hemiacetal and 3-keto-7-hydroxy forms of the compound.

13. A compound of claim 1 wherein M is hydrogen, an alkali metal, an alkaline earth metal, Al, Co, Ni, Zn or Cu.

14. A composition for controlling and preventing plant diseases caused by phytopathogenic microorganisms which comprises an effective amount of a compound of claim 1, together with a suitable carrier.

15. A composition according to claim 14, in which R is methyl and R$_o$ is halogen, —N$_3$, —SH, —OH or OY.

16. A method of controlling or preventing plant diseases caused by phytopathogenic microorganisms, which comprises the step of applying an effective amount of at least one compound of the formula I according to claim 1 to the plant, to parts of the plant or to the locus of the plant.

17. A method according to claim 16, where the plant disease is caused by fungi.

* * * * *